(12) United States Patent
Masure et al.

(10) Patent No.: US 7,022,818 B1
(45) Date of Patent: Apr. 4, 2006

(54) RAT NEUROTROPHIC FACTOR RECEPTOR, GFRα-4

(75) Inventors: Stefan L. J. Masure, Beerse (BE); Miroslav Cik, Beerse (BE); Evert W. Hoefnagel, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/019,337

(22) PCT Filed: Mar. 26, 2000

(86) PCT No.: PCT/EP00/04918

§ 371 (c)(1),
(2), (4) Date: Dec. 19, 2001

(87) PCT Pub. No.: WO01/02557

PCT Pub. Date: Jan. 11, 2001

(30) Foreign Application Priority Data

Jun. 29, 1919 (GB) .................................... 9915200

(51) Int. Cl.
*C07K 14/71* (2006.01)
(52) U.S. Cl. ..................................................... 530/350
(58) Field of Classification Search ................ 530/350; 514/12; 930/10
See application file for complete search history.

(56) References Cited

FOREIGN PATENT DOCUMENTS

| WO | WO 97/33912 A2 | 9/1997 |
|---|---|---|
| WO | WO 99/14235 A1 | 3/1999 |
| WO | WO 99/50298 A1 | 10/1999 |
| WO | WO 00/05375 A2 | 2/2000 |

OTHER PUBLICATIONS

Rudinger, In "Peptide Hormones", (ed. J.A. Parsons) Universisty Park Press, Baltimore (1976).*
Jane Thompson, Epaminondas Doxakis, Luzia G.P. Pinon, Philip Strachan, Anna Buj-Bello, Sean Wyatt, Vladimir L. Buchman, and Alun M. Davies, "GFRα-4, a New GDNF Family Receptor", Mol. Cell. Neudrosci. 11, 117-126(1998).
Yasushi Enokido, Fred De Sauvage, Jo-Anne Hong, Natalia Ninkina, Arnon Rosenthal, Vladimir L. Buchman and Alun M. Davies, "GRFα-4 and the tyrosine kinase Ret form a functional receptor complex for persephin", Current Biology 8, 1019-1022(1998).
Mart Saarma, Hannu Sariola, "Other Neurotrophic Factors: Gliat Cell Line-Derived Neurotrophic Factor (GDNF)", Microscopy Research and Technique, 45:292-302(1999).
Teresa M. Gunn, Kimberly A. Miller, Lin He, Richard W. Hyman, Ronald W. Davis, Arezou Azarani, Stuart F. Schlossman, Jonathan S. Duke-Cohan, Gregory S. Barsh, "The mouse mahongany locus encodes a tansmembrane form of human attractin", Nature vol. 398, 152-156,(1999).
Maria De Fatima Bonaldo, Gregory Lennon, and Marcelo Bento Soares, "Normalization and Substraction: Two Approaches to Facilitate Gene Discovery", Genome Research, 6:791-806,(1996).
Maria Lindahl, Tonis Timmusk, Jari Rossi, Mart Saarma, Matti S.Airaksinen, "Expression and Alternative Splicing of Mouse Gfra4 Suggest Roles in Endocrine Cell Development", Molecular and Cellular Neuroscience 15, 522-533(2000).
Stefan Masure, Miroslav Cik, Evert Hoefnagel, Christopher A. Nosrat, Ilse Van Der Linden, Rizaldy Scott, Paul Van Gompel, Anne S. J. Lesage, Peter Verhasselt, Carlos F. Ibanez, Robert D.Gordon, "Mammalian GFRα-4, a divergent member of the GFRα family of coresceptors for GDNF family ligands, is a receptors for the neurotrophic factor persephin", American Society for Biochemistry and Molecular Biology, Inc., 1-36(2000).
Matti S. Airaksinen, Alexey Titievskky, Mart Saarma, GDNF Family Neurotrophic Factor Signaling: Four Masters, One Servant?, Molecular and Cellular Neuroscience 13, 313-325(1999).

* cited by examiner

*Primary Examiner*—Robert C. Hayes
(74) *Attorney, Agent, or Firm*—Laura Donnelly

(57) ABSTRACT

There is disclosed a novel mammalian receptor protein designated GFRα-4 and the nucleic acid sequence encoding therefor. Also provided is an expression vector comprising the nucleic acid sequence and host cells transformed or transfected with the vector. Host cells expressing the receptor may be used to identify agonists or antagonists in relation to the receptor.

1 Claim, 5 Drawing Sheets

```
rGFRa-5(A) : MLSGAYLRVLNERPGQAVLWSLGCQRGSASSTEGNRCVEAEACTADEQC :  50
rGFRa-5(B) : MLSGAYLRVLNERPGQAVLWSLGCQRGSASSTEGNRCVEAEACTADEQC :  50 rGFRa-5(A) : QQLRSEYVAQCLGRAGWRGPGSCVRSRCRRALRFFARGPPALTHALLFC : 100
rGFRa-5(B) : QQLRSEYVAQCLGRAGWRGPGSCVRSRCRRALRFFARGPPALTHALLFC : 100 rGFRa-5(A) : GCEGPACAERRRQTFAPACAFSGPQLAPPSCLKPLDRCERSRRCRPRLFA : 150
rGFRa-5(B) : GCEGPACAERRRQTFAPACAFSGPQLAPPSCLKPLDRCERSRRCRPRLFA : 150 rGFRa-5(A) : FQASCAPAPGSRDGCPEEGGPRNCLRAYAGLVGTVVTPNYLDNVSARVAPW : 200
rGFRa-5(B) : FQASCAPAPGSRDGCPEEGGPRNCLRAYAGLVGTVVTPNYLDNVSARVAPW : 200 rGFRa-5(A) : CGCEASGNRREECEAFRKLFTRNPCLDGAIQAFDSSQPSVLQDQWNPYQN : 250
rGFRa-5(B) : CGCEASGNRREECEAFRKLFTRNPCLDGAIQAFDSSQPSVLQDQWNPYQN : 250 rGFRa-5(A) : AGCCFLWVSSMSILTALALQALL : 273
rGFRa-5(B) : AGQAKVEA--------------- : 258
```

Fig 5
A
B
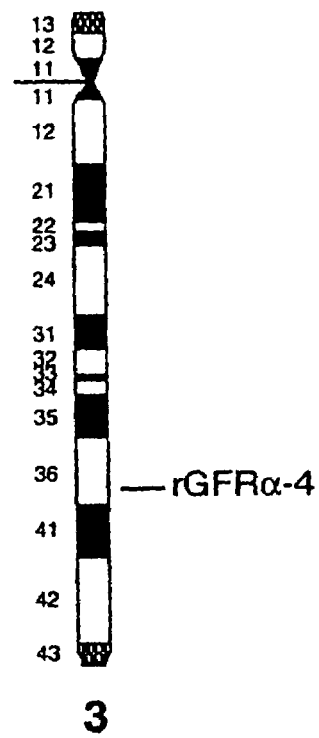
rGFRα-4
3

SEQUENCE LISTING

```
<160> NUMBER OF SEQ ID NOS: 48

<210> SEQ ID NO 1
<211> LENGTH: 792
<212> TYPE: DNA
<213> ORGANISM: Mus musculus
<220> FEATURE:
<221> NAME/KEY: modified_base
<222> LOCATION: (583)
<223> OTHER INFORMATION: a, c, g, t, unknown, or other
<220> FEATURE:
<221> NAME/KEY: modified_base
<222> LOCATION: (611)
<223> OTHER INFORMATION: a, c, g, t, unknown, or other
<220> FEATURE:
<221> NAME/KEY: modified_base
<222> LOCATION: (637)
<223> OTHER INFORMATION: a, c, g, t, unknown, or other
<220> FEATURE:
<221> NAME/KEY: modified_base
<222> LOCATION: (664)
<223> OTHER INFORMATION: a, c, g, t, unknown, or other
<220> FEATURE:
<221> NAME/KEY: modified_base
<222> LOCATION: (684)
<223> OTHER INFORMATION: a, c, g, t, unknown, or other
<220> FEATURE:
<221> NAME/KEY: modified_base
<222> LOCATION: (689)
<223> OTHER INFORMATION: a, c, g, t, unknown, or other
<220> FEATURE:
<221> NAME/KEY: modified_base
<222> LOCATION: (728)
<223> OTHER INFORMATION: a, c, g, t, unknown, or other
<220> FEATURE:
<221> NAME/KEY: modified_base
<222> LOCATION: (734)
<223> OTHER INFORMATION: a, c, g, t, unknown, or other
<220> FEATURE:
<221> NAME/KEY: modified_base
<222> LOCATION: (742)
<223> OTHER INFORMATION: a, c, g, t, unknown, or other
```

<400> SEQUENCE: 1

| | | | | | |
|---|---|---|---|---|---|
| gtgcgccgag | cgccggcgcc | agactttcgc | gcccgcctgc | gcgttctccg | gcccggggtt | 60 |
| ggtgccgccc | tcttgcctgg | agcccctgga | gcgctgcgag | cgcagccgcc | tgtgccggtg | 120 |
| cgtgcgtgcg | gggcgggctg | ggccgctcac | ccgcgtccgg | gcgcgcgcag | gccccgtctc | 180 |
| cttgccttcc | aggcctcatg | cgctcccgcg | cccggctccc | gcgaccgctg | cccggaggag | 240 |
| gggggcccgc | gttgtctgcg | cgtctacgca | ggcctcatgg | gcaccgtggt | cacccccaac | 300 |
| tacctggaca | acgtgagcgc | gcgcgttgcg | ccctggtgcg | gctgtgcggc | cagtggaaac | 360 |
| cggcgcgaag | aatgcgaagc | cttccgcaag | ctctttacaa | ggaaccctg | cttgggtgag | 420 |
| ggggcctgga | ggtcccgggg | aaccacggat | gtctgtggcc | caatccaagc | tgcctggccc | 480 |
| gtgggtctta | tttacgtcgc | atcatgtttt | gtgtgggcga | tggacaatgt | gcacatgcca | 540 |
| tggtacgtgg | gtggaagtca | agcgttaaaa | cgtgccaat | ggnctggaag | ttggccttcc | 600 |
| ttttgacact | natggggtgg | gccttttcttc | atggtgngcc | caacttaccct | ttggttggtc | 660 |
| ttgnctctgg | gtgggaatgg | cttnaattnc | agaattttgg | gggtcttgtt | tgaagcctgg | 720 |
| cttttgcnct | taanaacttg | anaagttaaa | ctcttattaa | tcccaatggg | gttcacctgt | 780 |
| aaagggagag | gg | | | | | 792 |

<210> SEQ ID NO 2
<211> LENGTH: 497
<212> TYPE: DNA
<213> ORGANISM: Mus musculus

<400> SEQUENCE: 2

| | | | | | |
|---|---|---|---|---|---|
| gtggaaccgg | cgcgaagaat | gcgaaccttc | cgcaagctct | ttacaaggaa | cccctgcttg | 60 |
| gatggtgcca | tacaagcctt | tgacagcttg | cagccatcag | ttctgcagga | ccagactgct | 120 |
| gggtgctgtt | tcccgcgggc | aaggcacgag | tggcctgaga | agagctggag | gcagaaacag | 180 |
| tccttgtttt | gtcctaacgc | ccaaggtgtc | ctggctgtat | gcactcactg | ccctggctct | 240 |
| ccaggccctg | ctctgattag | gaacatgaac | cgtggacgac | acagctgact | gccatgtctc | 300 |
| ccgatgactg | ctcactgagc | tgaaactccc | ttgccctcag | gtctgctgcc | cttttgcaggc | 360 |
| ctggacccct | gtgtggctgt | cctctggatt | ggggctgga | ggctagggtc | tgactgaaaa | 420 |
| gcctgtgttc | ccgtcagtag | gcatcttgtc | cattttcttc | cccatcctag | agctgagcac | 480 |
| ccatagatga | ggcctca | | | | | 497 |

<210> SEQ ID NO 3
<211> LENGTH: 901
<212> TYPE: DNA
<213> ORGANISM: Rattus rattus

<400> SEQUENCE: 3

| | | | | | |
|---|---|---|---|---|---|
| ggcaccgtgg | tcaccccaa | ctacctggac | aacgtgagcg | cgcgcgttgc | gccctggtgc | 60 |
| ggctgtgagg | ccagcggaaa | ccggcgcgaa | gagtgcgaag | ccttccgcaa | gcttttttaca | 120 |
| aggaacccct | gcttggatgg | tgccatacaa | gcctttgaca | gctcgcaacc | atcagttctg | 180 |
| caggaccagt | ggaaccccta | ccagaatgct | gggtgctgtt | tcctgtgggt | gtcctcgatg | 240 |
| tccatactca | ctgccctggc | tctccaggcc | ctgctctaat | taggaaggtg | aaccatggac | 300 |
| aacacagctg | actgccatgt | ctctggatta | tgctcactga | actgaaactc | ccttgccctc | 360 |
| aggtctgctg | tccttttgcag | ttctggaccc | ctgcatggct | gtctcctgga | ctgggagctg | 420 |
| gaggctaggg | cccgactgtt | aggttcccct | gttagtaggc | atctcgcctg | ttttcttcac | 480 |

-continued

```
catccttgag atgatggtag atgatattta gcacctgtag acagggcctc attgggcccc     540
ttgggcttac agagcagaac agagactagc ctcctgctct tagaattggg tagtgttctt     600
ttccaagaag acatggcact aaggcgatca tatgaacaga ctgacagact gcagtctaaa     660
tacccatgcc ccagggccag cgctgacctt gcttgtcacc tatgacatgg cgctgtgtag     720
ggattaaaga gagagattca ggtccctcct gctggacatc ccactggcct cccagactct     780
cccagcacct gcagtggcac agcagctcaa taaacccatg tgcactggaa aaaaaaaaa     840 aaaaaaaaaa aaaaaaaaaa aaaaaaaaaa aaaaaaaaaa aaaagaaaaa aaaaaaaaa     900 a                                                                     901
```

<210> SEQ ID NO 4
<211> LENGTH: 872
<212> TYPE: DNA
<213> ORGANISM: Rattus rattus

<400> SEQUENCE: 4

```
gtatggggag aggatgtgga gttggcagtt tctcatcgtt cccttctgta tttacccttc      60
tcaggcaggc caaggtggag gcctgagtgg cctgagaaga gatggaggca gaaacggtcc     120
ccgttttgtc ccaaggtgtc ctcgatgtcc atactcactg ccctggctct ccaggccctg     180
ctctaattag gaaggtgaac catggacaac acagctgact gccatgtctc tggattatgc     240
tcactgaact gaaactccct tgccctcagg tctgctgtcc tttgcagttc tggacccctg     300
catggctgtc tcctggactg ggagctggag gctagggccc gactgttagg ttcccctgtt     360
agtaggcatc tcgcctgttt tcttcaccat ccttgagatg atggtagatg atatttagca     420
cctgtagaca gggcctcatt gggccccttg gcttacaga gcagaacaga gactagcctc     480
ctgctcttag aattgggtag tgttcttttc caagaagaca tggcactaag gcgatcatat     540
gaacagactg acagactgca gtctaaatac ccatgcccca gggccagcgc tgaccttgct     600
tgtcacctat gacatggcgc tgtgtaggga ttaaagagag agattcaggt ccctcctgct     660
ggacatccca ctggcctccc agactctccc agcacctgca gtggcacagc agctcaataa     720
acccatgtgc actggaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaagaaa aaaaaaaaaa aa                                   872
```

<210> SEQ ID NO 5
<211> LENGTH: 2522
<212> TYPE: DNA
<213> ORGANISM: Rattus rattus

<400> SEQUENCE: 5

```
ctggtaagct ttaaggcaga ggagacctaa gagctgagac atgctatgtt gagtggagcg      60
tatttacggg tgctgaatga gaggccaggc caggcagttt tatggagtct tggatgccag     120
agaggtaagg aggtgggaaa ggaagtacta taaacctgaa tttggtgact ggctggatt     180 tgcatatgtc cagtgccaag ttcagacata gctgccgggt ttactgatgc tactctccca     240
aggtcaggca ttctattttc ccctgaatgg cttttcatct gtgacttatc tacatcttca     300
ctgaaactac tggtaaacgt ccaggtctgt ctcagggcga agtccatggg tctgccatta     360
agcctcagtg tcctgtcagg tgaagctggg gaggatggaa ggggtccagt agacgctctg     420
tgatgcatgt gccagttctg gagatggtgg tggaggctga acctgagctt ctggggaacc     480
```

```
tccgagtact gcctccattc acgacctggg tggatatccc taggacctgc ccatgcccgc    540
ttcctcagga aaacgggtc acgcctatgg gccacactct ctccccttgg gtttgggtat     600
```

```
tccgagtact gcctccattc acgacctggg tggatatccc taggacctgc ccatgcccgc    540
ttcctcagga aaacgggtc  acgcctatgg gccacactct ctccccttgg gtttgggtat    600
ctgcccccag ccccgccaa  attccggggt gtggaatgtg gagaaccaag cacagagggc    660
tgcagcctgc cctcccctca ccagggtcag cgagctccac tgaggggaat cgctgcgtgg    720
aagcagccga ggcgtgcaca gcagacgagc agtgccagca gctgcgctcc gagtacgtgg    780
cgcaatgcct gggccgggcg ggctggcggg gacccgggag ctgcgtgcgc tcccgctgcc    840
gccgtgccct cgccgcttc  ttcgcccgcg ggcctccggc gctcacgcac gcgctgctct    900
tctgcggatg cgaaggcccc cgcgtgcgcc agcgccggcg ccagacattc gcgcccgcct    960
gcgcgttctc cggccccag  ctggcgccac cttcctgcct gaagcccttg accgctgcg    1020
agcgaagccg ccggtgccgg tgcgtgcggg gcgggctggg ccgctcaccg gcgtccgggc   1080
gcgcgcaggc cccgtctctt tgccttccag gcctcatgcg ctcccgcgcc cggctcccgc   1140
gacggctgtc cggaggaggg gggcccgcgg tgtctgcgcg cctacgcagg ccttgtaggt   1200
acgctgggcg gcctctggcg ggcggggcgg cggaggcaga ttccggggc  ccgtcacagg   1260
tcctgggggt ccctgcaggc accgtggtca cccccaacta cctggacaac gtgagcgcgc   1320
gcgttgcgcc ctggtgcggc tgtgaggcca gcggaaaccg gcgcgaagag tgcgaagcct   1380
tccgcaagct ttttacaagg aaccctgct  tgggtgaggg ggctggagag cccgggcaac   1440
caaggacgtc tatggcccag tctaggctgc ctggcctgtg gggacccta  aaatgttttc   1500
gtcgtgtcgt atttggtgtg ggtgatggac agtgtgcacg tgccatggtg catgggtgga   1560
agtcagagga caacttgtca gtctctttct accacgtggg tccccgggat agcactgggc   1620
tcatcagttt tggtggcaag tgcctttgcc tgctgagcca tcttgctggc tgatgtgagc   1680
acattttga  tggaaagaaa ctgaggtttc cagagaccag atagccgatc actagagaat   1740
tcgagagatg tcaagaatct cttagggcta gaaaggatga gttaaaacat gtccaatgac   1800
ctggagttgg ccaaggctcc cttttggcact actgaggtct tttcctccat gtgttcccaa   1860
tttaacgctg ctgttcttgc ctcgggatga aatagcgttg ttccagattt ctgggggccc   1920
ggtttgaagc ctgtctctgc cacttcgtag ccgagagtta aactcttatt aatcctaatt   1980
gtgttcacct gtaagggcgg ggtgtgcact tgtcaacctc actcttagca cagtgacctt   2040
ccatctcagg ccgtgccttg cagattccag ggggtgtctc attttgtctc aagggagtgg   2100
agctgtttct agggtttcct ggccaaacct tctctggatc tctccactcc atagatggtg   2160
ccatacaagc ctttgacagc tcgcaaccat cagttctgca ggaccagtgg aaccctacc    2220
agaatgctgg gtgctgtttc ctgtgggtag gtatggggag aggatgtgga gttggcagtt   2280
tctcatcgtt cccttctgta tttacccttc tcaggcaggc caaggtggag gcctgagtgg   2340
cctgagaaga gatggaggca gaaacggtcc ccgttttgtc ccaaggtgtc ctcgatgtcc   2400
atactcactg ccctggctct ccaggccctg ctctaattag gaaggtgaac catggacaac   2460
acagctgact gccatgtctc tggattatgc tcactgaact gaaactccct tgccctcagg   2520
tc                                                                  2522
```

<210> SEQ ID NO 6
<211> LENGTH: 953
<212> TYPE: DNA
<213> ORGANISM: Rattus rattus

<400> SEQUENCE: 6

```
ctggtaagct ttaaggcaga ggagacctaa gagctgagac atgctatgtt gagtggagcg     60
```

```
tatttacggg tgctgaatga gaggccaggc caggcagttt tatggagtct tggatgccag      120
agagggtcag cgagctccac tgaggggaat cgctgcgtgg aagcagccga ggcgtgcaca      180
gcagacgagc agtgccagca gctgcgctcc gagtacgtgg cgcaatgcct gggccgggcg      240
ggctggcggg gacccgggag ctgcgtgcgc tcccgctgcc gccgtgccct cgccgcttc       300 ttcgcccgcg ggcctccggc gctcacgcac gcgctgctct tctgcggatg cgaaggcccc      360
gcgtgcgccg agcgccggcg ccagacattc gcgcccgcct gcgcgttctc cggcccccag      420
ctggcgccac cttcctgcct gaagcccttg gaccgctgcg agcgaagccg ccggtgccgg      480
ccccgtctct ttgccttcca ggcctcatgc gctcccgcgc ccggctcccg cgacggctgt      540
ccggaggagg ggggcccgcg tgtctgcgc gcctacgcag gccttgtagg caccgtggtc       600
acccccaact acctggacaa cgtgagcgcg cgcgttgcgc cctggtgcgg ctgtgaggcc      660
agcggaaacc ggcgcgaaga gtgcgaagcc ttccgcaagc ttttttacaag gaacccctgc     720 ttggatggtg ccatacaagc ctttgacagc tcgcaaccat cagttctgca ggaccagtgg      780 aaccccctacc agaatgctgg gtgctgtttc ctgtgggtgt cctcgatgtc catactcact    840
gccctggctc tccaggccct gctctaatta ggaaggtgaa ccatggacaa cacagctgac      900
tgccatgtct ctggattatg ctcactgaac tgaaactccc ttgccctcag gtc            953

<210> SEQ ID NO 7
<211> LENGTH: 1008
<212> TYPE: DNA
<213> ORGANISM: Rattus rattus

<400> SEQUENCE: 7
ctggtaagct ttaaggcaga ggagacctaa gagctgagac atgctatgtt gagtggagcg       60
tatttacggg tgctgaatga gaggccaggc caggcagttt tatggagtct tggatgccag      120
agagggtcag cgagctccac tgaggggaat cgctgcgtgg aagcagccga ggcgtgcaca      180
gcagacgagc agtgccagca gctgcgctcc gagtacgtgg cgcaatgcct gggccgggcg      240
ggctggcggg gacccgggag ctgcgtgcgc tcccgctgcc gccgtgccct cgccgcttc       300 ttcgcccgcg ggcctccggc gctcacgcac gcgctgctct tctgcggatg cgaaggcccc      360
gcgtgcgccg agcgccggcg ccagacattc gcgcccgcct gcgcgttctc cggcccccag      420
ctggcgccac cttcctgcct gaagcccttg gaccgctgcg agcgaagccg ccggtgccgg      480
ccccgtctct ttgccttcca ggcctcatgc gctcccgcgc ccggctcccg cgacggctgt      540
ccggaggagg ggggcccgcg tgtctgcgc gcctacgcag gccttgtagg caccgtggtc       600
acccccaact acctggacaa cgtgagcgcg cgcgttgcgc cctggtgcgg ctgtgaggcc      660
agcggaaacc ggcgcgaaga gtgcgaagcc ttccgcaagc ttttttacaag gaacccctgc     720 ttggatggtg ccatacaagc ctttgacagc tcgcaaccat cagttctgca ggaccagtgg      780 aaccccctacc agaatgctgg gcaggccaag gtggaggcct gagtggcctg agaagagatg    840
gaggcagaaa cggtccccgt tttgtcccaa ggtgtcctcg atgtccatac tcactgccct      900
ggctctccag gccctgctct aattaggaag gtgaaccatg gacaacacag ctgactgcca      960
tgtctctgga ttatgctcac tgaactgaaa ctcccttgcc ctcaggtc                  1008

<210> SEQ ID NO 8
<211> LENGTH: 273
<212> TYPE: PRT
<213> ORGANISM: Rattus rattus
```

-continued

```
<400> SEQUENCE: 8

Met Leu Ser Gly Ala Tyr Leu Arg Val Leu Asn Glu Arg Pro Gly Gln
 1               5                  10                  15

Ala Val Leu Trp Ser Leu Gly Cys Gln Arg Gly Ser Ala Ser Ser Thr
            20                  25                  30

Glu Gly Asn Arg Cys Val Glu Ala Ala Glu Ala Cys Thr Ala Asp Glu
        35                  40                  45

Gln Cys Gln Gln Leu Arg Ser Glu Tyr Val Ala Gln Cys Leu Gly Arg
    50                  55                  60

Ala Gly Trp Arg Gly Pro Gly Ser Cys Val Arg Ser Arg Cys Arg Arg
65                  70                  75                  80

Ala Leu Arg Arg Phe Phe Ala Arg Gly Pro Pro Ala Leu Thr His Ala
                85                  90                  95

Leu Leu Phe Cys Gly Cys Glu Gly Pro Ala Cys Ala Glu Arg Arg Arg
            100                 105                 110

Gln Thr Phe Ala Pro Ala Cys Ala Phe Ser Gly Pro Gln Leu Ala Pro
        115                 120                 125

Pro Ser Cys Leu Lys Pro Leu Asp Arg Cys Glu Arg Ser Arg Arg Cys
    130                 135                 140

Arg Pro Arg Leu Phe Ala Phe Gln Ala Ser Cys Ala Pro Ala Pro Gly
145                 150                 155                 160

Ser Arg Asp Gly Cys Pro Glu Glu Gly Pro Arg Cys Leu Arg Ala
                165                 170                 175

Tyr Ala Gly Leu Val Gly Thr Val Val Thr Pro Asn Tyr Leu Asp Asn
            180                 185                 190

Val Ser Ala Arg Val Ala Pro Trp Cys Gly Cys Glu Ala Ser Gly Asn
        195                 200                 205

Arg Arg Glu Glu Cys Glu Ala Phe Arg Lys Leu Phe Thr Arg Asn Pro
    210                 215                 220

Cys Leu Asp Gly Ala Ile Gln Ala Phe Asp Ser Ser Gln Pro Ser Val
225                 230                 235                 240

Leu Gln Asp Gln Trp Asn Pro Tyr Gln Asn Ala Gly Cys Cys Phe Leu
                245                 250                 255

Trp Val Ser Ser Met Ser Ile Leu Thr Ala Leu Ala Leu Gln Ala Leu
            260                 265                 270

Leu

<210> SEQ ID NO 9
<211> LENGTH: 258
<212> TYPE: PRT
<213> ORGANISM: Rattus rattus

<400> SEQUENCE: 9

Met Leu Ser Gly Ala Tyr Leu Arg Val Leu Asn Glu Arg Pro Gly Gln
 1               5                  10                  15

Ala Val Leu Trp Ser Leu Gly Cys Gln Arg Gly Ser Ala Ser Ser Thr
            20                  25                  30

Glu Gly Asn Arg Cys Val Glu Ala Ala Glu Ala Cys Thr Ala Asp Glu
        35                  40                  45

Gln Cys Gln Gln Leu Arg Ser Glu Tyr Val Ala Gln Cys Leu Gly Arg
    50                  55                  60

Ala Gly Trp Arg Gly Pro Gly Ser Cys Val Arg Ser Arg Cys Arg Arg
65                  70                  75                  80

Ala Leu Arg Arg Phe Phe Ala Arg Gly Pro Pro Ala Leu Thr His Ala
```

```
                        85                  90                  95
Leu Leu Phe Cys Gly Cys Glu Gly Pro Ala Cys Ala Glu Arg Arg Arg
                100                 105                 110

Gln Thr Phe Ala Pro Ala Cys Ala Phe Ser Gly Pro Gln Leu Ala Pro
        115                 120                 125

Pro Ser Cys Leu Lys Pro Leu Asp Arg Cys Glu Arg Ser Arg Arg Cys
    130                 135                 140

Arg Pro Arg Leu Phe Ala Phe Gln Ala Ser Cys Ala Pro Ala Pro Gly
145                 150                 155                 160

Ser Arg Asp Gly Cys Pro Glu Glu Gly Gly Pro Arg Cys Leu Arg Ala
                165                 170                 175

Tyr Ala Gly Leu Val Gly Thr Val Val Thr Pro Asn Tyr Leu Asp Asn
                180                 185                 190

Val Ser Ala Arg Val Ala Pro Trp Cys Gly Cys Glu Ala Ser Gly Asn
                195                 200                 205

Arg Arg Glu Glu Cys Glu Ala Phe Arg Lys Leu Phe Thr Arg Asn Pro
        210                 215                 220

Cys Leu Asp Gly Ala Ile Gln Ala Phe Asp Ser Ser Gln Pro Ser Val
225                 230                 235                 240

Leu Gln Asp Gln Trp Asn Pro Tyr Gln Asn Ala Gly Gln Ala Lys Val
                245                 250                 255

Glu Ala

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgcgttgtct gcgcgtctac g                                          21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggcgcgaag aatgcgaagc                                            20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cacccacgta ccatggcatg tgc                                        23

<210> SEQ ID NO 13
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
gtggtcaccc ccaactacct gg                                              22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccttccgca agctttttac aagg                                            24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctcttctgc ggatgcgaag gc                                              22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agctgccggg tttactgatg ctac                                            24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatgctactc tcccaaggtc aggc                                            24

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggtaagct ttaaggcaga ggagacc                                         27

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 19
catggcagtc agctgtgttg tcc                                              23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagctgtgtt gtccatggtt cacc                                             24

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tggttgcgag ctgtcaaagg cttgtatggc                                       30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggttcctt gtaaaaagct tgcggaaggc                                       30

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtccaaggg cttcaggcag gaagg                                            25

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccttcgcat ccgcagaaga gc                                               22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 25
ccaggtagtt gggggtgacc acg                                              23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccaggcatt gcgccacgta                                                  20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cattgcgcca cgtactcgga gc                                               22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gacctgaggg caagggagtt tca                                              23

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaagggagt ttcagttcag tgagc                                            25

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccatcctaat acgactcact atagggc                                          27

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 31
actcactata gggctcgagc ggc                                                       23

<210> SEQ ID NO 32
<211> LENGTH: 431
<212> TYPE: PRT
<213> ORGANISM: Gallus gallus

<400> SEQUENCE: 32

```
Met Arg Gly Ile Leu Tyr Phe Cys Thr Leu Ile Leu Glu Gly Met
 1               5                  10                  15

Ala Glu Ala Val Ser Ser Arg Asp Cys Leu Gln Ala Gly Glu Ser
                20                  25                  30

Cys Thr Asn Asp Pro Ile Cys Ser Ser Lys Phe Arg Thr Leu Arg Gln
            35                  40                  45

Cys Ile Ala Gly Asn Gly Ala Asn Lys Leu Gly Pro Asp Ala Lys Asn
        50                  55                  60

Gln Cys Arg Ser Thr Val Thr Ala Leu Leu Ser Ser Gln Leu Tyr Gly
 65                  70                  75                  80

Cys Lys Cys Lys Arg Gly Met Lys Lys Glu Lys His Cys Leu Ser Val
                85                  90                  95

Tyr Trp Ser Ile His His Thr Leu Met Glu Gly Met Asn Val Leu Glu
                100                 105                 110

Ser Ser Pro Tyr Glu Pro Phe Ile Arg Gly Phe Asp Tyr Val Arg Leu
            115                 120                 125

Ala Ser Ile Thr Ala Gly Ser Glu Asn Glu Val Thr Gln Val Asn Arg
        130                 135                 140

Cys Leu Asp Ala Ala Lys Ala Cys Asn Val Asp Glu Met Cys Gln Arg
145                 150                 155                 160

Leu Arg Thr Glu Tyr Val Ser Phe Cys Ile Arg Arg Leu Ala Arg Ala
                165                 170                 175

Asp Thr Cys Asn Arg Ser Lys Cys His Lys Ala Leu Arg Lys Phe Phe
            180                 185                 190

Asp Arg Val Pro Pro Glu Tyr Thr His Glu Leu Leu Phe Cys Pro Cys
        195                 200                 205

Glu Asp Thr Ala Cys Ala Glu Arg Arg Arg Gln Thr Ile Val Pro Ala
210                 215                 220

Cys Ser Tyr Glu Ser Lys Glu Lys Pro Asn Cys Leu Ala Pro Leu Asp
225                 230                 235                 240

Ser Cys Arg Glu Asn Tyr Val Cys Arg Ser Arg Tyr Ala Glu Phe Gln
                245                 250                 255

Phe Asn Cys Gln Pro Ser Leu Gln Thr Ala Ser Gly Cys Arg Arg Asp
            260                 265                 270

Ser Tyr Ala Ala Cys Leu Leu Ala Tyr Thr Gly Ile Ile Gly Ser Pro
        275                 280                 285

Ile Thr Pro Asn Tyr Ile Asp Asn Ser Thr Ser Ser Ile Ala Pro Trp
        290                 295                 300

Cys Thr Cys Asn Ala Ser Gly Asn Arg Gln Glu Glu Cys Glu Ser Phe
305                 310                 315                 320

Leu His Leu Phe Thr Asp Asn Val Cys Leu Gln Asn Ala Ile Gln Ala
                325                 330                 335

Phe Gly Asn Gly Thr Tyr Leu Asn Ala Ala Thr Ala Pro Ser Ile Ser
            340                 345                 350

Pro Thr Thr Gln Met Tyr Lys Gln Glu Arg Asn Ala Asn Arg Ala Ala
```

```
                355                 360                 365
Ala Thr Leu Ser Glu Asn Ile Phe Glu His Leu Gln Pro Thr Lys Val
    370                 375                 380

Ala Gly Glu Glu Arg Leu Leu Arg Gly Ser Thr Arg Leu Ser Ser Glu
385                 390                 395                 400

Thr Ser Ser Pro Ala Ala Pro Cys His Gln Ala Ala Ser Leu Leu Gln
                405                 410                 415

Leu Trp Leu Pro Pro Thr Leu Ala Val Leu Ser His Phe Met Met
                420                 425                 430
```

<210> SEQ ID NO 33
<211> LENGTH: 397
<212> TYPE: PRT
<213> ORGANISM: Mus musculus

<400> SEQUENCE: 33

```
Met Gly Leu Ser Trp Ser Pro Arg Pro Leu Leu Met Ile Leu Leu
  1               5                  10                  15

Leu Val Leu Ser Leu Trp Leu Pro Leu Gly Ala Gly Asn Ser Leu Ala
             20                  25                  30

Thr Glu Asn Arg Phe Val Asn Ser Cys Thr Gln Ala Arg Lys Lys Cys
         35                  40                  45

Glu Ala Asn Pro Ala Cys Lys Ala Ala Tyr Gln His Leu Gly Ser Cys
     50                  55                  60

Thr Ser Ser Leu Ser Arg Pro Leu Pro Leu Glu Glu Ser Ala Met Ser
 65                  70                  75                  80

Ala Asp Cys Leu Glu Ala Ala Glu Gln Leu Arg Asn Ser Ser Leu Ile
                 85                  90                  95

Asp Cys Arg Cys His Arg Arg Met Lys His Gln Ala Thr Cys Leu Asp
            100                 105                 110

Ile Tyr Trp Thr Val His Pro Ala Arg Ser Leu Gly Asp Tyr Glu Leu
        115                 120                 125

Asp Val Ser Pro Tyr Glu Asp Thr Val Thr Ser Lys Pro Trp Lys Met
    130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
                165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
        195                 200                 205

Ala Gln Gly Leu Leu Leu Cys Pro Cys Ala Pro Glu Asp Ala Gly Cys
    210                 215                 220

Gly Glu Arg Arg Arg Asn Thr Ile Ala Pro Ser Cys Ala Leu Pro Ser
225                 230                 235                 240

Val Thr Pro Asn Cys Leu Asp Leu Arg Ser Phe Cys Arg Ala Asp Pro
                245                 250                 255

Leu Cys Arg Ser Arg Leu Met Asp Phe Gln Thr His Cys His Pro Met
            260                 265                 270

Asp Ile Leu Gly Thr Cys Ala Thr Glu Gln Ser Arg Cys Leu Arg Ala
        275                 280                 285

Tyr Leu Gly Leu Ile Gly Thr Ala Met Thr Pro Asn Phe Ile Ser Lys
    290                 295                 300
```

```
Val Asn Thr Thr Val Ala Leu Ser Cys Thr Cys Arg Gly Ser Gly Asn
305                 310                 315                 320

Leu Gln Asp Glu Cys Glu Gln Leu Glu Arg Ser Phe Ser Gln Asn Pro
                325                 330                 335

Cys Leu Val Glu Ala Ile Ala Ala Lys Met Arg Phe His Arg Gln Leu
                340                 345                 350

Phe Ser Gln Asp Trp Ala Asp Ser Thr Phe Ser Val Val Gln Gln Gln
                355                 360                 365

Asn Ser Asn Pro Ala Leu Arg Leu Gln Pro Arg Leu Pro Ile Leu Ser
            370                 375                 380

Phe Ser Ile Leu Pro Leu Ile Leu Leu Gln Thr Leu Trp
385                 390                 395

<210> SEQ ID NO 34
<211> LENGTH: 444
<212> TYPE: PRT
<213> ORGANISM: Rattus rattus

<400> SEQUENCE: 34

Met Ile Leu Ala Asn Ala Phe Cys Leu Phe Phe Phe Leu Asp Glu Thr
1               5                   10                  15

Leu Arg Ser Leu Ala Ser Pro Ser Ser Leu Gln Gly Ser Glu Leu His
                20                  25                  30

Gly Trp Arg Pro Gln Val Asp Cys Val Arg Ala Asn Glu Leu Cys Ala
            35                  40                  45

Ala Glu Ser Asn Cys Ser Ser Arg Tyr Arg Thr Leu Arg Gln Cys Leu
        50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
                100                 105                 110

His Leu Gly Leu Thr Glu Gly Glu Glu Phe Tyr Glu Ala Ser Pro Tyr
            115                 120                 125

Glu Pro Val Thr Ser Arg Leu Ser Asp Ile Phe Arg Leu Ala Ser Ile
130                 135                 140

Phe Ser Gly Thr Gly Thr Asp Pro Ala Val Ser Thr Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Gln Thr Ile Leu Pro Ser
225                 230                 235                 240

Cys Ser Tyr Glu Asp Lys Glu Lys Pro Asn Cys Leu Asp Leu Arg Ser
                245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
        275                 280                 285
```

-continued

```
Asn Tyr Gln Ala Cys Leu Gly Ser Tyr Ala Gly Met Ile Gly Phe Asp
    290                 295                 300

Met Thr Pro Asn Tyr Val Asp Ser Asn Pro Thr Gly Ile Val Val Ser
305                 310                 315                 320

Pro Trp Cys Asn Cys Arg Gly Ser Gly Asn Met Glu Glu Cys Glu
                325                 330                 335

Lys Phe Leu Arg Asp Phe Thr Glu Asn Pro Cys Leu Arg Asn Ala Ile
                340                 345                 350

Gln Ala Phe Gly Asn Gly Thr Asp Val Asn Met Ser Pro Lys Gly Pro
            355                 360                 365

Ser Leu Pro Ala Thr Gln Ala Pro Arg Val Glu Lys Thr Pro Ser Leu
370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
            420                 425                 430

Ser Lys Lys Val Ile Lys Leu Asn Ser Gly Ser Ser
435                 440
```

<210> SEQ ID NO 35
<211> LENGTH: 468
<212> TYPE: PRT
<213> ORGANISM: Rattus rattus

<400> SEQUENCE: 35

```
Met Phe Leu Ala Thr Leu Tyr Phe Ala Leu Pro Leu Leu Asp Leu Leu
1               5                   10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175

Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
```

```
                210             215             220
Arg Arg Gln Thr Ile Val Pro Val Cys Ser Tyr Glu Glu Arg Glu Arg
225                 230                 235                 240

Pro Asn Cys Leu Ser Leu Gln Asp Ser Cys Lys Thr Asn Tyr Ile Cys
                245                 250                 255

Arg Ser Arg Leu Ala Asp Phe Phe Thr Asn Cys Gln Pro Glu Ser Arg
            260                 265                 270

Ser Val Ser Asn Cys Leu Lys Glu Asn Tyr Ala Asp Cys Leu Leu Ala
        275                 280                 285

Tyr Ser Gly Leu Ile Gly Thr Val Met Thr Pro Asn Tyr Val Asp Ser
290                 295                 300

Ser Ser Leu Ser Val Ala Pro Trp Cys Asp Cys Ser Asn Ser Gly Asn
305                 310                 315                 320

Asp Leu Glu Asp Cys Leu Lys Phe Leu Asn Phe Lys Asp Asn Thr
                325                 330                 335

Cys Leu Lys Asn Ala Ile Gln Ala Phe Gly Asn Gly Ser Asp Val Thr
            340                 345                 350

Met Trp Gln Pro Ala Pro Val Gln Thr Thr Thr Ala Thr Thr Thr
        355                 360                 365

Thr Ala Phe Arg Val Lys Asn Lys Pro Leu Gly Pro Ala Gly Ser Glu
370                 375                 380

Asn Glu Ile Pro Thr His Val Leu Pro Pro Cys Ala Asn Leu Gln Ala
385                 390                 395                 400

Gln Lys Leu Lys Ser Asn Val Ser Gly Ser Thr His Leu Cys Leu Ser
                405                 410                 415

Asp Ser Asp Phe Gly Lys Asp Gly Leu Ala Gly Ala Ser Ser His Ile
            420                 425                 430

Thr Thr Lys Ser Met Ala Ala Pro Pro Ser Cys Ser Leu Ser Ser Leu
        435                 440                 445

Pro Val Leu Met Leu Thr Ala Leu Ala Ala Leu Ser Val Ser Leu
450                 455                 460

Ala Glu Thr Ser
465

<210> SEQ ID NO 36
<211> LENGTH: 13
<212> TYPE: DNA
<213> ORGANISM: Rattus rattus

<400> SEQUENCE: 36
gaggtaagga ggt                                                          13

<210> SEQ ID NO 37
<211> LENGTH: 13
<212> TYPE: DNA
<213> ORGANISM: Rattus rattus

<400> SEQUENCE: 37
ccctcaccag ggt                                                          13

<210> SEQ ID NO 38
<211> LENGTH: 13
<212> TYPE: DNA
<213> ORGANISM: Rattus rattus

<400> SEQUENCE: 38
ccggtgcgtg cgg                                                          13
```

```
<210> SEQ ID NO 39
<211> LENGTH: 13
<212> TYPE: DNA
<213> ORGANISM: Rattus rattus

<400> SEQUENCE: 39
gcgcgcgcag gcc                                                          13

<210> SEQ ID NO 40
<211> LENGTH: 13
<212> TYPE: DNA
<213> ORGANISM: Rattus rattus

<400> SEQUENCE: 40
taggtacgct ggg                                                          13

<210> SEQ ID NO 41
<211> LENGTH: 13
<212> TYPE: DNA
<213> ORGANISM: Rattus rattus

<400> SEQUENCE: 41
gtccctgcag gca                                                          13

<210> SEQ ID NO 42
<211> LENGTH: 13
<212> TYPE: DNA
<213> ORGANISM: Rattus rattus

<400> SEQUENCE: 42
tgggtgaggg ggc                                                          13

<210> SEQ ID NO 43
<211> LENGTH: 13
<212> TYPE: DNA
<213> ORGANISM: Rattus rattus

<400> SEQUENCE: 43
cactccatag atg                                                          13

<210> SEQ ID NO 44
<211> LENGTH: 13
<212> TYPE: DNA
<213> ORGANISM: Rattus rattus

<400> SEQUENCE: 44
cgggtaggta tgg                                                          13

<210> SEQ ID NO 45
<211> LENGTH: 13
<212> TYPE: DNA
<213> ORGANISM: Rattus rattus

<400> SEQUENCE: 45
tgggtgctgt ttc                                                          13

<210> SEQ ID NO 46
<211> LENGTH: 13
<212> TYPE: DNA
<213> ORGANISM: Rattus rattus

<400> SEQUENCE: 46
```

|  |  |
|---|---|
| ttgtcccaag gtg | 13 |

<210> SEQ ID NO 47
<211> LENGTH: 13
<212> TYPE: DNA
<213> ORGANISM: Rattus rattus

<400> SEQUENCE: 47

|  |  |
|---|---|
| cccttctcag gca | 13 |

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 48

His His His His His His
 1               5

RAT NEUROTROPHIC FACTOR RECEPTOR, GFRα-4

CROSS REFERENCE TO RELATED APPLICATIONS

This Application is a National Stage of International Application of PCT/EP00/04918 filed May 26, 2000 which claims priority from Great Britain Patent Application No. 9915200.1 filed Jun. 29, 1999 and entitled "Neurotrophic Factor Receptor."

BACKGROUND OF THE INVENTION

The present invention is concerned with cloning and expression of a novel mammalian receptor protein, designated herein GFRα-4 and in particular with an isolated nucleic acid sequence encoding the GFRα-4 protein, an expression vector comprising said nucleic acid sequence, a host cell transformed or transfected with said vector, isolated GFRα4 protein, compounds which act as agonists or antagonists in relation to GFRα-4 and methods of identifying them, together with pharmaceutical compositions comprising the isolated nucleic acid, the receptor protein or said agonist or antagonist.

Neurotrophic growth factors are involved in neuronal differentiation, development and maintenance. These proteins can prevent degeneration and promote survival of different types of neuronal cells and are thus potential therapeutic agents for neurodegenerative diseases. Glial cell-line derived neurotrophic factor (GDNF) was the first member of a growing subfamily of neurotrophic factors structurally distinct from the neurotrophins. GDNF is a distantly related member of the transforming growth factor β (TGF-β) superfamily of growth factors, characterized by a specific pattern of seven highly conserved cysteine residues within the amino acid sequence (Kingsley, 1994). GDNF was originally purified using an assay based on its ability to maintain the survival and function of embryonic ventral midbrain dopaminergic neurons in vitro (Lin et al., 1993). Other neuronal cell types in the central (CNS) or peripheral nervous systems (PNS) have been shown to be responsive to the survival effects of GDNF (Henderson et al., 1994, Buj-Bello et al., 1995, Mount et al., 1995, Oppenheim et al., 1995). GDNF is produced by cells in an inactive proform, which is cleaved specifically at a RXXR recognition site to produce active GDNF (Lin et al., 1993). In view of its effects on dopaminergic neurons, clinical trials have evaluated GDNF as a possible treatment for Parkinson's disease, a common neurodegenerative disorder characterized by the loss of a high percentage (up to 70%) of dopaminergic cells in the substantia nigra of the brain. Exogenous administration of GDNF has potent protective effects in animal models of Parkinson's disease (Henderson et al., 1994, Beck et al., 1995, Tomac et al., 1995, Yan et al., 1995, Gash et al., 1996, Choi-Lundberg et al., 1997, Bilang-Bleuel et al., 1997, Mandel et al., 1997).

Recently, three new members of the GDNF family of neurotrophic factors have been discovered. Neurturin (NTN) was purified from conditioned medium from Chinese hamster ovary (CHO) cells using an assay based on the ability to promote the survival of sympathetic neurons in culture (Kotzbauer et al., 1996). The mature neurturin protein is 57% similar to mature GDNF. Persephin (PSP) was discovered by degenerate primer PCR using genomic DNA. The mature protein, like mature GDNF, promotes the survival of ventral midbrain dopaminergic neurons and of motor neurons in culture (Milbrandt et al., 1998). The similarity of the mature persephin protein with mature GDNF and neurturin is 50%. Very recently, a fourth member has been cloned using genomic DNA information in the public EMBL database and has been named Enovin (EVN) (Masure et al., 1999) or Artemin (ARTN) (Baloh et al., 1998b). This factor is ±57% similar to NTN and PSP and acts primarily on peripheral neurons.

All four GDNF family members require a heterodimeric receptor complex in order to carry out downstream intracellular signal transduction. GDNF binds to the GDNF family receptor alpha 1 (GFRα-1; also termed GDNFRα, RETL1 or TrnR1; GFRαNomenclature Committee, 1997) subunit, a glycosyl phosphatidyl inositol (GPI)-anchored membrane protein (Jing et al., 1996, Treanor et al., 1996, Sanicola et al., 1997). The GDNF/GFRα-1 complex subsequently binds to and activates the cRET proto-oncogene, a membrane bound tyrosine kinase (Durbec et al., 1996, Trupp et al., 1996), resulting in phosphorylation of tyrosine residues in cRET and subsequent activation of downstream signal transduction pathways (Worby et al., 1996). GFRα-2 (also termed RETL2, NTNR-α, GDNFR-β or TrnR2), which is similar to GFRα-1, has been identified by a number of different groups (Baloh et al., 1997, Sanicola et al., 1997, Klein et al., 1997, Buj-Bello et al., 1997, Suvanto et al., 1997). The human GFRα-1 and GFRα-2 receptor subunits are 49% identical and 63% similar by protein sequence with 30 of the 31 cysteine residues conserved. Both receptors contain a hydrophobic domain at their carboxy-termini involved in GPI anchoring to the membrane. GFRα-1 and GFRα-2 are widely expressed in almost all tissues and expression may be developmentally regulated (Sanicola et al., 1997, Widenfalk et al., 1997).

GFRα-1 is the preferred receptor for GDNF, whereas GFRα-2 preferentially binds neurturin (Jing et al., 1996, Treanor et al., 1996, Klein et al., 1997). It is also clear, however, that there is some cross-talk between these growth factors and receptors as GDNF can bind to GFRα-2 in the presence of cRET (Sanicola et al., 1997) and neurturin can bind to GFRα-1 with low affinity (Klein et al., 1997). GDNF and neurturin are thus part of a neurotrophic signalling system whereby different ligand-binding subunits (GFRα-1 and GFRα-2) can interact with the same tyrosine kinase subunit (cRET).

Recently, a third member of the GFRα family of coreceptors, GFRα-3, has been described (Jing et al., 1997, Masure et al., 1998, Worby et al., 1998, Naveilhan et al., 1998, Baloh et al., 1998a). This receptor's amino acid sequence is 35% identical to both GFRα-1 and GFRα-2. GFRα-3 is not expressed in the developing or adult CNS, but is highly expressed in several developing and adult sensory and sympathetic ganglia of the PNS (Widenfalk et al., 1998, Naveilhan et al., 1998, Baloh et al., 1998a). GFRα-3 has been shown to be the preferred coreceptor for Enovin/artemin and also signals via cRET (Masure et al., 1999, Baloh et al., 1998b). Crosstalk between EVN/ARTN and GFRα-1 seems also possible, at least in vitro.

A fourth member of the GFRα family has been identified in chicken (Thompson et al., 1998) and has been shown to mediate signalling of persephin via cRET (Enokido et al., 1998). A functional mammalian homologue encoding a mammalian persephin receptor has yet to be discovered.

The present inventors have surprisingly identified a further novel mammalian receptor of the GDNF family designated herein as GFRα-4. The DNA sequence has been cloned and a number of splice variants encoding the receptor have also been identified.

SUMMARY OF THE INVENTION

Accordingly, there is provided by the present invention an isolated or substantially pure form of a nucleic acid encoding a mammalian GDNF family receptor α-4 designated GFRα-4. The nucleic acid molecule is preferably from rat, mouse or human. Preferably, the receptor encoded by said nucleic acid molecule comprises the amino acid sequence illustrated in Sequence ID No's. 8 or 9 or encoding a functional equivalent, derivative or bioprecursor of said receptor.

Although initially, in view of the fact that only 4 members of the GFRαs were known, the new receptor has previously been called GFRα-5. However, it has now termed α-4 in order to comply with the existing nomenclature for GFRα family members and to indicate that the GFRα receptor of the present invention is the mammalian orthologue of the chicken GFRα-4 receptor.

BRIEF DESCRIPTION OF THE FIGURES

The present invention may be more clearly understood from the following exemplary embodiment with reference to the accompanying figures wherein;

FIG. 2: is an alignment of the predicted protein sequences of splice variants A and B of rat GFRα-4, (SEQ ID NOS: 8 and 9, respectively). The sequences of rat GFRα-4 splice variants A and B were aligned using the ClustalW alignment program (EMBL, Heidelberg, Germany). Amino acid residues conserved between the 2 variants are included in the black areas. Amino acid residues are numbered to the right. The dashes indicate gaps introduced into the sequence to optimize the alignment.

FIG. 3: is an alignment of the predicted protein sequences of GFRα family members. The sequence of rat GFRα-4 variants A and B (SEQ ID NOS: 8 and 9, respectively), rat GFRα-1 (SEQ ID NO: 35, EMBL acc. no. U59486), rat GFRα-2 (SEQ ID NO: 34, EMBL acc. no. AF003825), mouse GFRα-3 (SEQ ID NO: 33, EMBL acc. no. AB008833) and chicken GFRα-4 (SEQ ID NO: 32, EMBL acc. no. AF045162) were aligned using the ClustalW alignment program (EMBL, Heidelberg, Germany). Amino acid residues conserved between all 6 proteins are included in the black areas. Residues conserved between 4 or 5 of the sequences are shaded in grey. Cysteine residues conserved between all six GFRα's are indicated with an asterisk above the sequence. Amino acid residues are numbered to the right. The dashes indicate gaps introduced into the sequence to optimize the alignment.

FIG. 5. The rat GFRα-4 gene is localized on chromosome 3q36. A mixture of two rat GFRα-4 probes was used for FISH analysis. (A) Double-spot FISH signals on the middle-distal part of rat chromosome 3 (arrows). (B) Position of the GFRα-4 gene locus on rat chromosome 3q36.

DETAILED DESCRIPTION OF THE INVENTION

Figure 1:
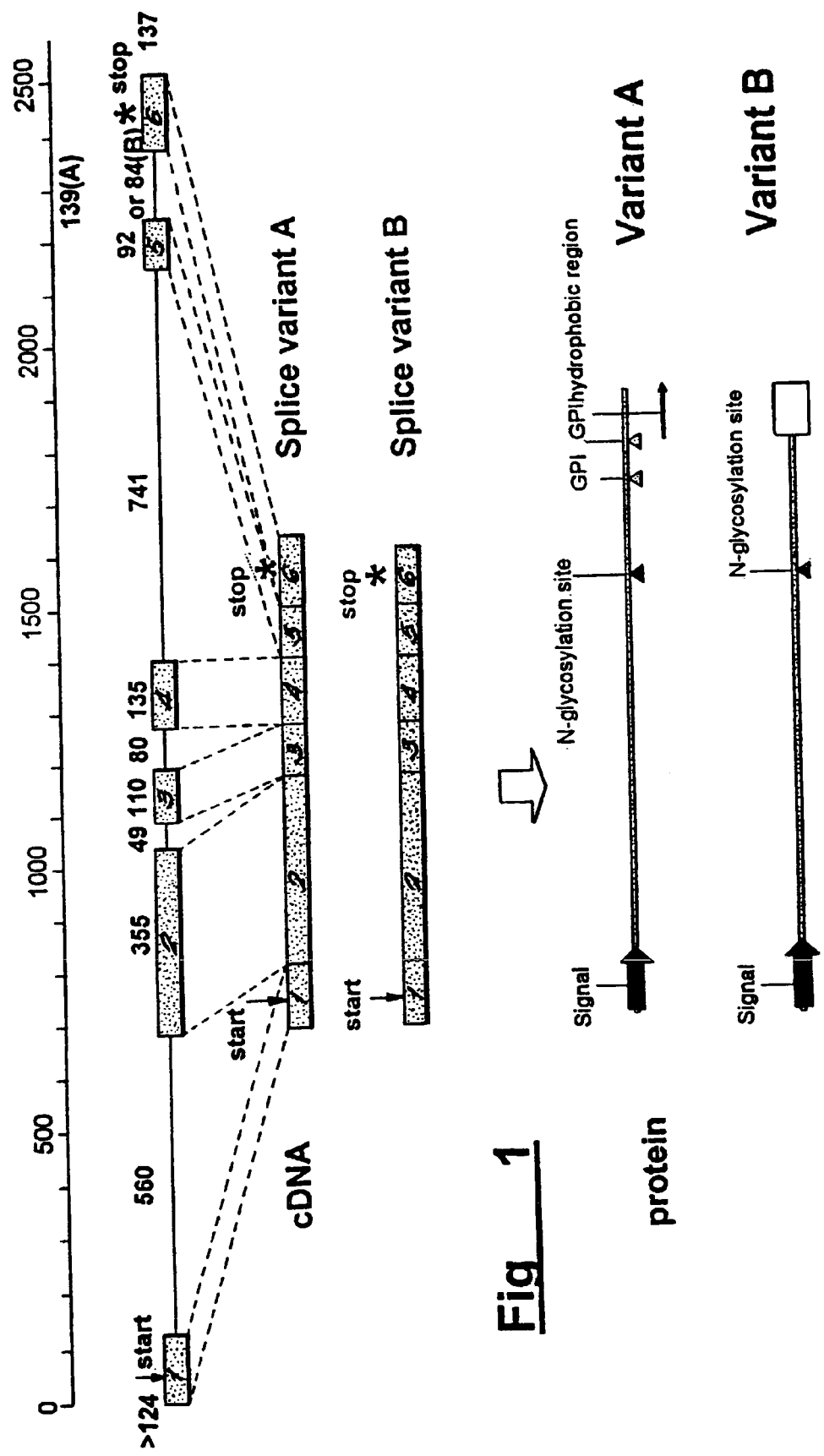
FIG. 1: is an illustration of the Structure of the rat GFRα-4 gene. The top line shows a scale in bp. The line below shows the genomic structure of the rat GFRα-4 gene. Exons are represented by boxes and numbered, intron sequences are depicted as lines. The sizes (in bp) of introns and exons are indicated above the diagram. The translation start codon is indicated by an arrow and the stop codon by an asterisk. The cDNA sequences of variants A and B obtained by splicing out the intron sequences is shown below the genomic sequence. Alternative splicing of intron 5 results in an earlier stop codon in splice variant B. The predicted protein sequences of variants A and B are shown at the bottom. The predicted signal peptide, a putative N-glycosylation site and a hydrophobic COOH-terminal region preceded by one or two possible sites for GPI-cleavage (in variant A only) are indicated on the diagrams.

Thus, the present invention relates to a nucleic acid molecule encoding a mammalian GDNF family receptor α-4 (GFRα-4) or an immunologically and/or biologically active fragment thereof, which comprises a nucleotide sequence selected from the group consisting of (a) nucleotide sequences encoding the polypeptide comprising the amino acid sequence depicted in SEQ ID NO: 8 or 9;

(b) nucleotide sequences comprising the coding sequence as depicted in SEQ ID NO: 5 or 6;

(c) nucleotide sequences encoding a polypeptide derived from the polypeptide encoded by a nucleotide sequence of (a) or (b) by way of substitution, deletion and/or addition of one or several amino acids of the amino acid sequence encoded by the nucleotide sequence of (a) or (b);

(d) nucleotide sequences the complementary strand of which hybridizes with a nucleotide sequence of any one of (a) to (c);

(e) nucleotide sequences encoding a polypeptide the amino acid sequence of which has an identity of 30% or more to the amino acid sequence of the polypeptide encoded by a nucleotide sequence of any one of (a) to (d);

(f) nucleotide sequences encoding a polypeptide capable of binding persephin comprising a fragment or an epitope-bearing portion of a polypeptide encoded by a nucleotide sequence of any one of (a) to (e);

(g) nucleotide sequences comprising at least 15 consecutive nucleotides of a nucleotide sequence of any one of (a) to (f) and encoding a polypeptide capable of binding persephin; and (h) nucleotide sequences comprising a nucleotide sequence which is degenerated as a result of the genetic code to a nucleotide sequence of any of (a) to (g).

Advantageously, the nucleic acid molecule according to the invention may be used for expression of said GFRα-4 protein in, for example, a host cell or the like, using an appropriate expression vector. Preferably, the nucleic acid molecule is a DNA molecule, and even more preferably a cDNA molecule having a sequence as illustrated in any of Sequence ID No's. 5 to 7 or the complement thereof. Alternatively, the nucleic acid molecule is capable of hybridising to the sequences of the invention under conditions of high stringency or to the complement thereof. Stringency of hybridisation as used herein refers to conditions under which polynucleic acids are stable. The stability of hybrids is reflected in the melting temperature (Tm) of the hybrids. Tm can be approximated by the formula:

$$81.5° C. + 16.6(\log_{10}[Na^+]) + 0.41(\% \, G\&C) - 600 l/1$$

wherein 1 is the length of the hybrids in nucleotides. Tm decreases approximately by 1–1.5° C. with every 1% decrease in sequence homology.

The nucleic acid capable of hybridising to nucleic acid molecules according to the invention will generally be at least 70%, preferably at least 80 or 90% and more preferably at least 95% homologous to the nucleotide sequences according to the invention.

Advantageously, the antisense molecule may be used as a probe or as a medicament or in a pharmaceutical composition together with a pharmaceutically acceptable carrier; diluent or excipient.

According to a second aspect of the invention, there is provided a DNA expression vector comprising the DNA molecule according to the invention. This vector may, advantageously, be used to transform or transfect a host cell to achieve expression of GFRα-4 according to the invention. Preferably, the DNA is included in a plasmid, for subsequent transfection or transformation of the host cell.

An expression vector according to the invention includes a vector having a nucleic acid according to the invention operably linked to regulatory sequences, such as promoter regions, that are capable of effecting expression of said DNA fragments. The term "operably linked" refers to a juxta position wherein the components described are in a relationship permitting them to function in their intended manner. Such vectors may be transformed into a suitable host cell to provide for expression of a polypeptide according to the invention. Thus, in a further aspect, the invention provides a process for preparing receptors according to the invention which comprises cultivating a host cell, transformed or transfected with an expression vector as described above under conditions to provide for expression by the vector of a coding sequence encoding the receptors, and recovering the expressed receptors.

The vectors may be, for example, plasmid, virus or phage vectors provided with an origin of replication, optionally a promoter for the expression of said nucleotide and optionally a regulator of the promoter. The vectors may contain one or more selectable markers, such as, for example, ampicillin resistance.

Regulatory elements required for expression include promoter sequences to bind RNA polymerase and transcription initiation sequences for ribosome binding. For example, a bacterial expression vector may include a promoter such as the lac promoter and for transcription initiation in the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

Nucleic acid molecules according to the invention may be inserted into the vectors described in an antisense orientation in order to provide for the production of antisense RNA. Antisense RNA or other antisense nucleic acids may be produced by synthetic means.

In accordance with the present invention, a defined nucleic acid includes not only the identical nucleic acid but also any amino base variations including, in particular, substitutions in bases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The present invention also advantageously provides nucleic acid sequences of at least approximately 10 contiguous nucleotides of a nucleic acid according to the invention and preferably from 10 to 50 nucleotides. These sequences may, advantageously, be used as probes or primers to initiate replication, or the like. Such nucleic acid sequences may be produced according to techniques well known in the art, such as, by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

According to the present invention these probes may be anchored to a solid support. Preferably, they are present on an array so that multiple probes can simultaneously hybridize to a single biological sample. The probes can be spotted onto the array or synthesised in situ on the array. (See Lockhart et al., Nature Biotechnology, vol. 14, December 1996 "Expression monitoring by hybridisation into high density oligonucleotide arrays"). A single array can contain more than 100, 500 or even 1,000 different probes in discrete locations.

The nucleic acid sequences, according to the invention may be produced using such recombinant or synthetic means, such as, for example, using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which bring about amplification of the desired region, isolating the amplified region or fragment and recovering the amplified DNA. Generally, such techniques as defined herein are well known in the art, such as described in Sambrook et al (Molecular Cloning: a Laboratory Manual, 1989). The nucleic acids or oligonucleotides according to the invention may carry a revealing label. Suitable labels include radioisotopes such as $^{32}P$ or $^{35}S$, enzyme labels or other protein labels such as biotin or fluorescent markers. Such labels may be added to the nucleic acids or oligonucleotides of the invention and may be detected using known techniques per se.

The present invention also comprises within its scope proteins or polypeptides encoded by the nucleic acid molecules according to the invention or a functional equivalent, derivative or bioprecursor thereof. Preferably, the protein comprises the amino acid sequence of Sequence ID No's. 8 and 9.

A "functional equivalent" as defined herein should be taken to mean a receptor that exhibits the same properties and functionality associated with the GFRα-4 receptor according to the invention. A "derivative" should be taken to mean a polypeptide or protein in which certain amino acids may have been altered or deleted or replaced and which polypeptide or protein retains biological activity of said GFRα-4 receptor and/or which can cross react with antibodies raised using a receptor according to the invention as the challenging antigen.

Encompassed within the scope of the invention are hybrid and modified forms of the GFRα-4 receptor according to the invention including fusion proteins and fragments. The hybrid and modified forms include, for example, when certain amino acids have been subjected to some modification or replacement, such as for example, by point mutation and yet which results in a protein which possesses the same receptor specificity as the GFRα-4 receptor of the invention.

In this context it is understood that the terms biological activity, receptor specificity and functional receptor (fragment) preferably include the ability to bind persephin, preferably specifically and that the GFRα-4 of the invention has no or substantially no binding activity on GDNF, NTN, and/or EVN/ART. The biological activity, receptor specificity and/or functionality, for example binding activity of the GFRα-4 of the invention, variants, derivatives and fragments thereof can be determined according methods well known in the art, preferably as described in the appended examples. Preferably, the $K_D$ of the GFRα-4 of the invention for persephin is 1 to $10 \times 10^{-9}$, particularly preferred $5.9 \pm 2.8 \times 10^{-9}$ when determined in accordance with the examples described below; see the description to Table 6.

The protein according to the invention should be taken to include all possible amino acid variants encoded by the nucleic acid molecule according to the invention including a polypeptide encoded by said molecule and having conservative amino acid changes. Proteins or polypeptides according to the invention further include variants of such sequences, including naturally occurring allelic variants which are substantially homologous to said proteins or polypeptides. In this context, substantial homology is regarded as a sequence which has at least 70%, and preferably 80 or 90% amino acid homology with the proteins or polypeptides encoded by the nucleic acid molecules according to the invention.

Substantial homology should be taken to mean that the nucleotide and amino acid sequences of the GFRα-4 of the invention display a certain degree of sequence identity. Preferably they share an identity of at least 30%, preferably 40%, more preferably 50%, still more preferably 60%, most preferably 70%, and particularly an identity of at least 80%, preferably more than 90% and still more preferably more than 95% is desired with respect to the nucleotide or amino acid sequences depicted in Seq. ID Nos. 5 to 9, respectively. A preferred method for determining the best overall match between a query sequence (a sequence of the present invention) and a subject sequence, also referred to as a global sequence alignment, can be determined using, for example, the FASTDB computer program based on the algorithm of Brutlag et al. (Comp. App. Biosci. 6 (1990), 237–245.) In a sequence alignment the query and subject sequences are both DNA sequences. An RNA sequence can be compared by converting U's to T's. The result of said global sequence alignment is in percent identity. Further programs that can be used in order to determine homology/identity are described below and in the examples. The sequences that are homologous to the sequences described above are, for example, variations of said sequences which represent modifications having the same biological function, in particular encoding proteins with the same or substantially the same receptor specificity, i.e. binding specificity. They may be naturally occurring variations, such as sequences from other mammals, or mutations. These mutations may occur naturally or may be obtained by mutagenesis techniques. The allelic variations may be naturally occurring allelic variants as well as synthetically produced or genetically engineered variants. In a preferred embodiment the sequences are derived from mouse, more preferable from human. These sequences can also be retrieved from existing databases with nucleotide sequences of yet unknown function. For example, a BLAST search on the EMBL database using the identified rat GFRα-4 sequences as query sequence yielded a genomic mouse sequence (accession no. AF155960) and a genomic human sequence (accession no. AC017113; containing contigs. derived from human genomic DNA) with parts almost identical with parts of the rat GFRα-4 sequence (exons 2, 3 and 4). These nucleotides sequences are also encompassed in the present invention.

A further aspect of the invention comprises the host cell itself transformed with the DNA expression vector described herein, which host cell preferably comprises a eukaryotic cell, which may be for example, a mammalian cell, an insect cell or yeast cell or the like. In one embodiment the cell comprises a human embryonic kidney cell and preferably a cell of the HEK293 cell line. Alternatively, the cell may comprise NIH/3T3 mouse fibroblasts or Chinese hamster ovary (CHO) cells or COS-7 cells.

Further provided by the present invention is a transgenic cell, tissue or organism comprising a transgene capable of expressing GFRα-4 according to the invention, or of expressing a functional equivalent, derivative or bioprecursor of said receptor. The term "transgene capable of expression" as used herein means a suitable nucleic acid sequence which leads to expression of a human receptor having the same function and/or activity as GFRα-4. The transgene may include, for example, genomic nucleic acid isolated from rat cells or synthetic nucleic acid, including cDNA, integrated into the genome or in an extra chromosomal state. Preferably, the transgene comprises the nucleic acid sequence encoding GFRα-4 according to the invention or a functional fragment of said nucleic acid. A functional fragment of said nucleic acid should be taken to mean a fragment of the gene or cDNA encoding GFRα-4 receptor or a functional equivalent or bioprecursor of said GFRα-4 which fragment is capable of being expressed to produce a functional receptor protein. For example, the gene may comprise deletions of mutations but may still encode a functional receptor.

Further provided by the present invention is an isolated or purified GFRα-4 protein having the amino acid sequence illustrated in Sequence ID No. 2 or a functional fragment or bioprecursor of said receptor or alternatively a GFRα-4 protein expressed by the transgenic cell, tissue or organism according to the invention. Also provided by the invention are membrane preparations from cells expressing GFRα-4.

The present invention is further directed to inhibiting GFRα-4 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature protein sequence, which encodes for the protein of the present invention, is used to design an antisense RNA oligonucleotide of from 10 to 40 base pairs in length. A DNA oligonucleotide is designed to be complementary to a region of the gene involved in transcription (triple-helix—see Lee et al. Nucl. Acids Res., 6:3073 (1979); Cooney et al., Science, 241:456 (1988); and Dervan et al., Science, 251: 1360 (1991), thereby preventing transcription and the production of GFRα-4. The antisense RNA oligonucleotide hybridises to the mRNA in vivo and blocks translation of an mRNA molecule into the GFRα-4 receptor.

Antibodies to the GFRα-4 receptor according to the invention are also provided which may be used in a medicament or in a pharmaceutical composition.

Antibodies to the GFRα-4 of the invention may, advantageously, be prepared by techniques which are known in the art. For example, polyclonal antibodies may be prepared by inoculating a host animal, such as a mouse, with the polypeptide according to the invention or an epitope thereof and recovering immune serum. Monoclonal antibodies may be prepared according to known techniques such as described by Kohler R. and Milstein C., Nature (1975) 256, 495–497.

Antibodies according to the invention may also be used in a method of detecting for the presence of GFRα-4 by reacting the antibody with a sample and identifying any protein bound thereto. A kit may also be provided for performing said method which comprises an antibody according to the invention and means for reacting the antibody with said sample.

Advantageously, the antibody according to the invention may also be used as a medicament or in the preparation of a medicament for treating diseases associated with expression of the GFRα-4 of the invention. The invention also further provides a pharmaceutical composition comprising said antibody together with a pharmaceutically acceptable carrier, diluent or excipient therefor.

Proteins which interact with the polypeptide of the invention may be identified by investigating protein—protein interactions using the two-hybrid vector system first proposed by Chien et al (1991), Proc. Natl. Acad. Sci. USA 88: 9578–9582.

This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as, a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein. Proteins which bind to the GFRα-4 receptor can be identified using this technique. The proteins identified can also be used to identify compounds which acts as agonists/antagonists of these proteins. The structure of the receptor can also be used to design agonists or antagonists of the receptor. The present invention also comprises an agonist or antagonist of the human GFRα-4 receptor according to the invention which agonist or antagonist advantageously may also be used as a medicament or in a pharmaceutical composition together with a pharmaceutically acceptable carrier diluent or excipient therefor.

Agonists or antagonists may be identified by contacting a cell expressing GFRα-4 with a compound to be tested and monitoring the degree of any GFRα-4 mediated functional or biological response, such as for example, by monitoring the level of phosphorylation in said cell or by cytosensor or ligand binding assays in the presence of cRET or similar proteins in the signal transduction pathway. Preferably, the cell may be a host cell or transgenic cell according to the invention as defined herein. Agonists and antagonists of GFRα-4 may also be identified by, for example, contacting a membrane preparation comprising GFRα-4 with the compound to be tested in the presence of cRET or other similar proteins involved in the signal transduction pathway of which GFRα-4 is a component and monitoring the interaction of GFRα-4 with cRET or said similar proteins. Advantageously, any compounds or molecules identified as agonists or antagonists in relation to GFRα-4 may themselves be used in a pharmaceutical composition as defined above or as a medicament.

Also provided by the invention are molecules or compounds that act on the signal transduction pathway of which GFRα-4 or a functional equivalent belong. Alternatively, the molecules may interfere with complex formation or interaction of GFRα-4 or its functional equivalent, with cRET or a similar protein in the signal transduction pathway of which GFRα-4 is a component.

Furthermore, the present invention relates to a method of producing an antagonist or agonist of GFRα-4 according to the invention comprising the steps of any one of the above described screening methods; and additionally
  (i) synthesizing the compound obtained or identified in said method or an physiologically acceptable analog or derivative thereof in an amount sufficient to provide said antagonist or agonist in a therapeutically effective amount to a patient; and/or
  (ii) combining the compound obtained or identified in said method or an analog or derivative thereof with a pharmaceutically acceptable carrier".

The compounds isolated by the above methods also serve as lead compounds for the development of analog compounds. The analogs should have a stabilized electronic configuration and molecular conformation that allows key functional groups to be presented to the GFRα-4 receptor in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used.

Compounds identified as agonists or antagonists in relation to GFRα-4 or as ligands or compounds which interfere with the signal transduction pathway of which GFRα-4 is a part, may advantageously be used in the preparation of a medicament for treatment of neurodegenerative diseases, such as, for example, Alzheimers disease, Parkinsons disease, Motor Neuron Disease, peripheral neuropathy, spinal cord injury, familial hirschsprung disease, in addition to various carcinomas such as for example in gastrointestinal cancer and also in treatment of diseases which may be associated with GFRα-4 dysfunction. Compounds identified as antagonists may, advantageously, be used in the preparation of a medicament for the treatment of carcinoma or in alleviating pain.

The present invention also further comprises a method of identifying ligands of GFRα-4 according to the invention, which method comprises contacting said receptor with either a cell extract or alternatively a compound to be tested for its potential as a GFRα-4 ligand, and isolating any molecules bound to GFRα-4.

A diagnostic kit is also provided by the present invention, which kit, comprises a probe including any of, a nucleic acid molecule encoding a GFRα-4 protein according to the invention, a molecule capable of hybridising thereto under high stringency conditions, a fragment of said nucleic acids, an antisense molecule according to the invention, together with means for contacting biological material to be tested with said nucleic acid probe. A diagnostic kit in accordance with the invention may also comprise an agonist or antagonist in relation to GFRα-4 or an antibody, preferably a monoclonal antibody to GFRα-4. Thus, advantageously, the kit may be used, as appropriate to identify, for example, cells expressing or lacking in said receptor or genetic defects or the like or for determining whether a compound is a agonist or an antagonist of GFRα-4 receptor. Kits for determining whether a compound is an agonist or an antagonist in relation to GFRα-4 may comprise a cell or membrane preparation expressing said receptor according to the present invention, means for contacting said cell with said compound and means for monitoring the level of any GFRα-4 mediated functional or biological response, by for example measuring the level of phosphorylation in said cell or by cytosensor or ligand binding assays in the presence of cRET or similar proteins involved in the signal transduction pathway of which GFRα-4 is a component.

This invention will be better understood by reference to the Experimental Details which follow, but those skilled in the art will readily appreciate that the specific experiments detailed are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXAMPLES

While the foregoing specification teaches the principles of the present invention, with examples provided for the purpose of illustration, it will be understoood that the practice of the invention encompasses all of the usual variations, adaptations and/or modifications as come within the scope of the following claims and their equivalents.

Oligonucleotide Synthesis for PCR and DNA Sequencing

All oligonucleotide primers used were ordered from Eurogentec (Seraing, Belgium). Insert-specific sequencing primers (15- and 16-mers) and primers for use in PCR reactions were designed manually. DNA was prepared on Qiagen-tip-20 or -100 anion exchange or Qiaquick spin columns (Qiagen GmbH, Düsseldorf, Germany) and recovered from the columns in 30 μl TE-buffer (10 mM Tris.HCl, 1 mM EDTA (sodium salt), pH 8.0). Sequencing reactions were done on both strands using the ABI prism BigDye Terminator Cycle sequencing kit and were run on an Applied Biosystems 377XL sequencer (Perkin Elmer, ABI Division, Foster City, Calif., USA). The Sequencher™ software was used for sequence assembly and manual editing (GeneCodes, AnnArbor, Mich., USA).

Identification of a cDNA Sequence Encoding a Novel Member of the GFRα Family

Using the human GFRα-1, GFRα-2 or GFRα-3 DNA or protein sequences as the query sequence, BLAST (Basic Local Alignment Search Tool; Altschul et al., 1990) searches were performed on the daily updates of the public EMBL database. A mouse EST (expressed sequence tag) sequence with EMBL accession number AU035938 showed homology to GFRα-1, GFRα-2 and GFRα-3. The smallest sum probabilities (SSP) obtained by the BLAST analyses are summarized in Table 1.

TABLE 1

BLAST results.

| Query sequence | DNA/PROTEIN | SSP |
|---|---|---|
| GFRα-1 | protein | 7.5e−25 |
| GFRα-2 | protein | 1.3e−12 |
| GFRα-3 | protein | 2.2e−20 |
| GFRα-1 | DNA | 6.6e−09 |
| GFRα-2 | DNA | >0.011 |
| GFRα-3 | DNA | 0.0096 |

AU035938 (sequence 1) is a sequence of 792 bp derived from a mouse brain cDNA library. To obtain consistent homology with other members of the GFRα family upon translation a frame shift has to be introduced near position 165 in the DNA sequence. It is not clear whether this is due to a sequencing error or whether there is another explanation. Using this EST sequence as the query sequence, the BLAST search against the public EMBL database was repeated. One additional clone (acc. no. AA823200; sequence 2) yielded a significant SSP of 1e-18. Upon inspection of this 497 bp clone, which was derived from a mouse mammary gland cDNA library, only the first 61 bp were identical with part of AU035938 (position 353 to 415). The rest of the sequence of AA823200 was different from AU035938, but contained parts of which the translated amino acid sequence showed homology with the other GFRα's. Therefore it was hypothesized that AU035938 and AA823200 could represent two variant forms of the same receptor, which was called GFRα-4.

Cloning of Mouse GFRα-4 cDNA

First, we tried to amplify a fragment of the mouse GFRα-4 cDNA on Marathon Ready™ cDNAs (Clontech Laboratories, Palo Alto, Calif., USA) derived from mouse brain and mouse embryo. Primers were designed using the EST sequences (EMBL acc. no. AU035938 and AA823200) to amplify a 274 bp fragment of mouse GFRα-4. The primers used for the amplification of mouse GFRα-4 are shown in the table below.

TABLE 2

Primers used for the amplification of mouse GFRα-4 DNA sequences.

| Name | Sequence | n |
|---|---|---|
| MOUSE-GFRα4-sp2 (SEQ ID NO:10) | CGCGTTGTCTGCGCGTCTACG | 21 |
| MOUSE-GFRα4-sp3 (SEQ ID NO:11) | CGGCGCGAAGAATGCGAAGC | 20 |
| MOUSE-GFRα4-ap2 (SEQ ID NO:12) | CACCCACGTACCATGGCATGTGC | 23 |

PCR reactions were done using the Taq polymerase system (Boehringer Mannheim, Mannheim, Germany). PCR reactions were performed in a total volume of 50 μl, containing 1× Taq PCR reaction buffer, 0.25 mM DNTP, 0.5 μM of primers MOUSE-GFRα4-sp2 and MOUSE-GFRα4-ap2, 1 μl of Taq polymerase and 2 μl of mouse embryo or mouse brain Marathon Ready™ cDNA. Samples were heated to 95° C. for 5 min and cycling was done for 30 s at 94° C., 1 min at 60° C. and 45 s at 72° C. for 35 cycles, with a final step of 7 min at 72° C. A semi-nested PCR was then performed on 1 µl of the primary PCR reaction with primers MOUSE-GFRα4-sp3 and MOUSE-GFRα4-ap2. PCR reactions were performed in a total volume of 50 µl, containing 1× Taq PCR reaction buffer, 0.25 mM DNTP, 0.5 µM of primers MOUSE-GFRα4-sp3 and MOUSE-GFRα4-ap2, 1 µl of Taq polymerase and 1 µl of primary PCR product. Samples were heated to 95° C. for 5 min and cycling was done for 30 s at 94° C., 1 min at 60° C. and 45 s at 72° C. for 35 cycles, with a final step of 7 min at 72° C. PCR products were analysed on a 1% (w/v) agarose gel in 1× TAE buffer (40 mM Tris-acetate, 1 mM EDTA (sodium salt), pH 8.3). A PCR fragment of the expected size (270 bp) was excised from the gel and purified with the Qiaquick gel extraction kit (Qiagen Gmbh, Hilden, Germany). The PCR fragments were sequenced to confirm their identity. The obtained sequence corresponded to the EST database sequences. In order to determine the upstream and downstream coding sequences of mouse GFRα-4, 5' and 3' RACE experiments were performed. Since these experiments did not work as expected and since, at some points, frame shifts had to be introduced in the mouse GFRα-4 sequence to yield consistent homology with other GFRα's after translation, we decided to shift to the cloning of the rat homologue of mouse GFRα-4.

Identification and Cloning of Rat GFRα-4 cDNA Sequences

The cDNA sequences with accession number AU035938 and AA823200 described above were used as the query sequence in BLAST searches on the proprietary LifeSeq and ZooSeq databases (Incyte Pharmaceuticals, Palo Alto, Calif., USA). Two rat clones with high homology to the mouse GFRα-4 sequences were identified: number 701290919H1 (270 bp; hit with AU035938 (SSP=1.1e–32) and with AA823200 (SSP=1.3e–21)) and number 701291473H1 (250 bp; hit only with AA823200 (SSP=4.3e–42)). From comparing the translated protein sequences derived from clones 701291473H1 and 701290919H1 to the known GFRα protein sequences, it could be deduced that sequence 701290919H1 was probably localised 5' to sequence 701291473H1 and that these sequences were almost adjacent to each other in the full GFRα-4 cDNA sequence. Therefore, two forward primers (RAT-GFRα4-sp1 and RAT-GFRα4-sp2) were designed in the 5' region of sequence 701290919H1 and two reverse primers (RAT-GFRα4-ap1 and RAT-GFRα4-ap2) in the 3' region of sequence 701291473H1. All primer sequences used in PCR experiments are summarized in Table 3.

TABLE 3

Primers used for the amplification of rat GFRα-4 sequences. The RACE-ap1 and RACE-ap2 primers are included in the Marathon Ready ™ cDNA kit.

| Name | Sequence | n |
| --- | --- | --- |
| RAT-GFRα4-sp1 (SEQ ID NO:13) | GTGGTCACCCCCAACTACCTGG | 22 |
| RAT-GFRα4-sp2 (SEQ ID NO:14) | GCCTTCCGCAAGCTTTTTACAAGG | 24 |
| RAT-GFRα4-sp3 (SEQ ID NO:15) | GCTCTTCTGCGGATGCGAAGGC | 22 |
| RAT-GFRα4-sp4 (SEQ ID NO:16) | AGCTGCCGGGTTTACTGATGCTAC | 24 |
| RAT-GFRα4-sp5 (SEQ ID NO:17) | GATGCTACTCTCCCAAGGTCAGGC | 24 |
| RAT-GFRα4-sp6 (SEQ ID NO:18) | CTGGTAAGCTTTAAGGCAGAGGAGACC | 27 |
| RAT-GFRα4-ap1 (SEQ ID NO:19) | CATGGCAGTCAGCTGTGTTGTCC | 23 |
| RAT-GFRα4-ap2 (SEQ ID NO:20) | CAGCTGTGTTGTCCATGGTTCACC | 24 |
| RAT-GFRα4-ap3 (SEQ ID NO:21) | TGGTTGCGAGCTGTCAAAGGCTTGTATGGC | 30 |
| RAT-GFRα4-ap4 (SEQ ID NO:22) | GGGGTTCCTTGTAAAAAGCTTGCGGAAGGC | 30 |
| RAT-GFRα4-ap5 (SEQ ID NO:23) | GGTCCAAGGGCTTCAGGCAGGAAGG | 25 |
| RAT-GFRα4-ap6 (SEQ ID NO:24) | GCCTTCGCATCCGCAGAAGAGC | 22 |
| RAT-GFRα4-ap7 (SEQ ID NO:25) | CCAGGTAGTTGGGGGTGACCACG | 23 |
| RAT-GFRα4-ap7b (SEQ ID NO:26) | CCCAGGCATTGCGCCACGTA | 20 |
| RAT-GFRα4-ap8 (SEQ ID NO:27) | CATTGCGCCACGTACTCGGAGC | 22 |
| RAT-GFRα4-ap9 (SEQ ID NO:28) | GACCTGAGGGCAAGGGAGTTTCA | 23 |
| RAT-GFRα4-ap10 (SEQ ID NO:29) | GCAAGGGAGTTTCAGTTCAGTGAGC | 25 |
| RACE-ap1 (SEQ ID NO:30) | CCATCCTAATACGACTCACTATAGGGC | 27 |
| RACE-ap2 (SEQ ID NO:31) | ACTCACTATAGGGCTCGAGCGGC | 23 |

A PCR was then performed using primers RAT-GFRα4-sp1 and RAT-GFRα4-ap1 on rat brain Quickclone cDNA (Clontech Laboratories, Palo Alto, Calif., USA) to confirm the presence of rat GFRα-4 in brain-derived cDNA. Since the DNA sequence coding for the rat GFRα-4 sequence has a high G+C content in this region, PCR reactions were done using the Advantage-GC PCR kit (Clontech). PCR reactions were performed in a total volume of 50 µl, containing 1× GC cDNA PCR reaction buffer, 0.2 mM DNTP, 1 M GC-MELTä, 200 nM of primers RAT-GFRα4-sp1 and RAT-GFRα4-ap1, 1 µl of Advantage KlenTaq polymerase mix and 1 µl of rat brain Quickclone cDNA. Samples were heated to 95° C. for 1 min and cycling was done for 1 min at 95° C., 1 min at 56° C. and 1 min at 72° C. for 30 cycles, with a final step of 7 min at 72° C. A nested PCR was then performed on 1 µl of the primary PCR reaction with primers RAT-GFRα4-sp2 and RAT-GFRα4-ap2. PCR reactions were performed in a total volume of 50 μl, containing 1× GC cDNA PCR reaction buffer, 0.2 mM dNTP, 1 M GC-MELTä, 200 nM of primers RAT-GFRα4-sp2 and RAT-GFRα4-ap2, 1 μl of Advantage KlenTaq polymerase mix and 1 μl of primary PCR product. Samples were heated to 95° C. for 1 min and cycling was done for 30 s at 95° C., 1 min at 56° C. and 1 min at 72° C. for 25 cycles, with a final step of 7 min at 72° C. PCR products were analysed on a 1% (w/v) agarose gel in 1× TAE buffer (40 mM Tris-acetate, 1 mM EDTA (sodium salt), pH 8.3). Two PCR fragments of approximately 1100 and 200 bp, respectively, were excised from the gel and purified with the Qiaquick gel extraction kit (Qiagen Gmbh, Hilden, Germany). The PCR fragments were sequenced to confirm their identity. The smallest fragment yielded a sequence of 211 bp corresponding to the joined sequences 701290919H1 and 701291473H1. The larger fragment yielded a sequence of 1049 bp of which 18 bp at the 5' end, 59 bp at the 3' end and an internal stretch of 92 bp corresponded to the sequence of the 211 bp fragment, but which had additional sequence stretches in between. This fragment represented a variant of rat GFRα-4.

Both clones 701291919H1 and 701291473H1 were obtained from Incyte Pharmaceuticals and the inserts completely sequenced. The sequences are included in this application (sequence 3=701290919H1 and sequence 4=701291473H1). Both clones were derived from the same 7-day old rat brain cortex cDNA library. Both clones differ in their 5' ends (first 134 bp in 701291473H1 and first 227 bp in 701290919H1) but are identical thereafter. Both contain part of the GFRα-4 coding sequence up to a stop codon (position 184–186 in 701291473H1 and 277–279 in 701290919H1). A 3' untranslated region of 549 bp followed by a poly(A)-tail is then present in both clones. We hypothesized that both clones are different variants of the rat GFRα-4 gene. Primers (RAT-GFRα4-ap3 and RAT-GFRα4-ap4) were designed on a part of the sequence common to both variants to perform 5' RACE experiments in order to determine the 5' end of the rat GFRα-4 cDNA. First, a 5' RACE PCR was performed on rat brain Marathon Ready™ cDNA (Clontech). PCR reactions were performed in a total volume of 50 μl, containing 1× GC cDNA PCR reaction buffer, 0.2 mM dNTP, 1 M or 1.5 M GC-MELTä, 200 nM of primers RAT-GFRα4-ap3 and RACE-ap1, 1 μl of Advantage KlenTaq polymerase mix and 5 μl of rat brain Marathon Ready™ cDNA. Samples were heated to 95° C. for 30 s and cycling was done for 30 s at 95° C., 4 min at 72° C. for 5 cycles, then 30 s at 95° C., 4 min at 70° C. for 5 cycles, then 30 s at 95° C., 4 min at 68° C. for 25 cycles, with a final step of 7 min at 68° C. A nested PCR was then performed on 1 μl of the primary PCR reaction with primers RAT-GFRαα4-ap4 and RACE-ap2. PCR reactions were performed in a total volume of 50 μl, containing 1× GC cDNA PCR reaction buffer, 0.2 mM DNTP, 1 M or 1.5 M GC-MELTä, 200 nM of primers RAT-GFRα4-ap4 and RACE-ap2, 1 μl of Advantage KlenTaq polymerase mix and 1 μl of primary PCR product. Cycling was done using exactly the same parameters as for the primary PCR. PCR products were analysed on a 1% (w/v) agarose gel in 1× TAE buffer (40 mM Tris-acetate, 1 mM EDTA (sodium salt), pH 8.3). A fragment of approximately 350 bp was excised from the gel and cloned into the plasmid vector pCR2.1-TOPO using the TOPO TA cloning kit according to manufacturer's instructions (Invitrogen BV, Leek, The Netherlands). One of the resulting clones yielded an insert sequence of 387 bp which extended the rat GFRα-4 sequence in the 5' direction. Upon translation, this additional cDNA sequence yielded a protein sequence without any internal stop codons and with substantial homology to the other known GFRα sequences. Since no putative ATG start codon could be detected within this additional sequence, novel primers (RAT-GFRα4-ap5 and RAT-GFRα4-ap6) were designed at the 5' end of this sequence to perform additional 5' RACE experiments. First, a 5' RACE PCR was performed on rat heart Marathon Ready™ cDNA (Clontech). PCR reactions were performed in a total volume of 50 μl, containing 1× GC cDNA PCR reaction buffer, 0.2 mM DNTP, 1 M GC-MELTä, 200 nM of primers RAT-GFRα4-ap5 and RACE-ap1, 1 μl of Advantage KlenTaq polymerase mix and 5 μl of rat heart Marathon Ready™ cDNA. Samples were heated to 95° C. for 30 s and cycling was done for 30 s at 95° C., 4 min at 72° C. for 5 cycles, then 30 s at 95° C., 4 min at 70° C. for 5 cycles, then 30 s at 95° C., 4 min at 68° C. for 25 cycles, with a final step of 7 min at 68° C. A nested PCR was then performed on 1 μl of the primary PCR reaction with primers RAT-GFRα4-ap6 and RACE-ap2. PCR reactions were performed in a total volume of 50 μl, containing 1× GC cDNA PCR reaction buffer, 0.2 mM DNTP, 1 M GC-MELTä, 200 nM of primers RAT-GFRα4-ap6 and RACE-ap2, 1 μl of Advantage KlenTaq polymerase mix and 1 μl of primary PCR product. Cycling was done using exactly the same parameters as for the primary PCR. PCR products were analysed on a 1% agarose gel. A fragment of approximately 200 bp was excised from the gel and cloned into the plasmid vector pCR2.1-TOPO using the TOPO TA cloning kit as described above. Sequencing of two resulting clones extended the rat GFRα-4 sequence with another 128 bp in the 5' direction. Based on this sequence, another primer set (RAT-GFRα4-ap7 and RAT-GFRα4-ap8) was designed to perform additional 5' RACE experiments. RACE PCR was performed on rat brain, heart and kidney Marathon Ready™ cDNA. PCR reactions were performed in a total volume of 50 μl, containing 1× GC cDNA PCR reaction buffer, 0.2 mM dNTP, 1 M GC-MELTä, 200 nM of primers RAT-GFRα4-ap7b and RACE-ap1, 1 μl of Advantage KlenTaq polymerase mix and 5 μl of rat heart, brain or kidney Marathon Ready™ cDNA. Samples were heated to 95° C. for 30 s and cycling was done for 30 s at 95° C., 4 min at 72° C. for 5 cycles, then 30 s at 95° C., 4 min at 70° C. for 5 cycles, then 30 s at 95° C., 4 min at 68° C. for 25 cycles, with a final step of 7 min at 68° C. A nested PCR was then performed on 1 μl of the primary PCR reaction with primers RAT-GFRα4-ap8 and RACE-ap2. PCR reactions were performed in a total volume of 50 μl, containing 1× GC cDNA PCR reaction buffer, 0.2 mM dNTP, 1 M GC-MELTä, 200 nM of primers RAT-GFRα4-ap8 and RACE-ap2, 1 μl of Advantage KlenTaq polymerase mix and 1 μl of primary PCR product. Cycling was done using exactly the same parameters as for the primary PCR. PCR products were analysed on a 1% agarose gel. Several fragments ranging in size from approximately 200 bp to 1200 bp were visible on the gel and were excised and cloned in vector pCR2.1-TOPO using TOPO-TA cloning. The inserts of several clones were sequenced. From these clones, the sequence of rat GFRα-4 could be extended in the 5' direction. Two different sequences were identified. One sequence extended the ratGFRα-4 sequence with 215 bp in the 5' direction and included an in-frame start codon preceded by an in-frame upstream stop codon. The resulting predicted protein sequence (52 additional amino acid residues) includes a predicted signal peptide of 29 amino acid residues (as determined by the SPScan program included in the Wisconsin package version 10.0, Genetics Computer Group (GCG), Madison, Wis., USA; score 7.0, probability 1.171e–02). The other sequence determined by these 5' RACE experiments extended the ratGFRα-4 sequence with 552 bp in the 5' direction and also included an in-frame start codon preceded by an in-frame upstream stop codon. The most 3' 79 base pairs of this novel sequence were identical to the 3' 79 base pairs of the 215 bp sequence, but the rest of the sequence was different. The resulting predicted protein sequence (113 additional amino acid residues), however, did not have a predicted signal peptide sequence at the NH$_2$-terminus (SPScan, GCG package). The different partial cDNA sequences resulting from the subsequent 5' RACE experiments together with the sequences from the Incyte database were compared and merged into several possible rat GFRα-4 variants. In order to identify which of the identified variants are real, primers were designed 5' of the translation start codon (primers RAT-GFRα4-sp4 and RAT-GFRα4-sp5 for the "long" 5' variant resulting from the 552 bp RACE fragment and RAT-GFRα4-sp6 for the "short" 5' variant resulting from the 215 bp RACE fragment) and 3' of the translation stop codon (RAT-GFRα4-ap9 and RAT-GFRα4-ap10). These primers were then used to amplify the full GFRα-4 coding sequences using cDNA derived from different rat tissues. First, sequences coding for the "long" 5' variant were amplified by PCR. PCR reactions were performed in a total volume of 50 μl, containing 1× GC cDNA PCR reaction buffer, 0.2 mM DNTP, 1 M GC-MELTä, 200 nM of primers RAT-GFRα4-sp4 and RAT-GFRα4-ap9, 1 μl of Advantage KlenTaq polymerase mix and 5 μl of rat heart, brain or kidney Marathon Ready™ cDNA. Samples were heated to 95° C. for 1 min and cycling was done for 45 s at 95° C., 1 min at 57° C. and 1 min at 72° C. for 35 cycles, with a final step of 7 min at 72° C. A nested PCR was then performed on the primary PCR reaction with primers RAT-GFRα4-sp5 and RAT-GFRα4-ap10. PCR reactions were performed in a total volume of 50 μl, containing 1× GC cDNA PCR reaction buffer, 0.2 mM dNTP, 1 M GC-MELTä, 200 nM of primers RAT-GFRα4-sp5 and RAT-GFRα4-ap10, 1 μl of Advantage KlenTaq polymerase mix and 1 μl of primary PCR product. Cycling was done using exactly the same parameters as for the primary PCR, except that 30 PCR cycles were done instead of 35. PCR products were analysed on a 1% agarose gel. Several fragments ranging in size from approximately 1000 to 1250 bp were excised from gel and cloned in vector pCR2.1-TOPO using TOPO-TA cloning. The inserts of several clones were sequenced. Next, sequences coding for the "short" 5' variant were amplified by PCR. PCR reactions were performed in a total volume of 50 μl, containing 1× GC cDNA PCR reaction buffer, 0.2 mM dNTP, 1 M GC-MELTä, 200 nM of primers RAT-GFRα4-sp6 and RAT-GFRα4-ap9, 1 μl of Advantage KlenTaq polymerase mix and 5 μl of rat heart Marathon Ready™ cDNA. Samples were heated to 95° C. for 5 min and cycling was done for 30 s at 94° C., 1 min at 57° C. and 2 min 30 s at 72° C. for 35 cycles, with a final step of 7 min at 72° C. PCR products were analysed on a 1% agarose gel. Several fragments ranging in size from approximately 1500 to 2200 bp were excised from gel and cloned in vector pCR2.1-TOPO using TOPO-TA cloning. The inserts of several clones were sequenced. Analysis of all the obtained sequences (16 resulting clones were completely sequenced) allowed the rat GFRα-4 DNA sequence to be divided into sequence stretches common to all identified variants, with 5 intervening sequence stretches present or absent depending on the variant. All 5 intervening sequences contain 5' and 3' splice site consensus sites (GT at the 5' end and AG at the 3' end of the intron sequence) (Senaphthy et al., 1990) (see table 4 below) and could thus potentially represent unspliced introns.

In order to strengthen the hypothesis that the identified variants could result from the conservation of unspliced introns in certain mRNA transcripts, the rat GFRα-4 sequence was compared to the genomic sequence of human GFRα-1 (Angrist et al., 1998). From this analysis, it was apparent that the GFRα-4 sequences common to all transcripts coincided with exons in GFRα-1 (see table 4 below). The intervening sequences absent in some transcripts coincided with intron sequences in human GFRα-1. Therefore, we considered all intervening sequences as unspliced introns. The intron present between exon 5 and exon 6 can be spliced out in two different ways and results in the presence of two different splice variants of rat GFRα-4, which we have called variant A and variant B.

Sequence 5 shows the consensus sequence for rat GFRα-4 including the intron sequences (intron 1: bp 125 to 684; intron 2: bp 1040 to 1088; intron 3: bp 1199 to 1278; intron 4: bp 1414 to 2154; intron 5A: bp 2247 to 2385 and intron 5B: bp 2231 to 2314). A polymorphism was detected at position 2244 in sequence 5, with T found in 50% of the sequenced clones and C in the other 50%. This polymorphism leads to an amino acid change in the protein (variant A) from W to R, in the hydrophobic region involved in GPI-anchoring. FIG. 1 schematically shows the structure of the rat GFRα-4 gene together with the derived cDNA for splice variants A and B after splicing out of the intron sequences and the translated protein sequences of variants A and B with their characteristics. Table 4 shows the DNA sequence at the intron-exon boundaries together with the sizes of identified introns and exons. The right column shows the sizes of the corresponding exons in the genomic sequence of human GFRα-1 (from Angrist et al., 1998).

TABLE 4

Intron-exon structure of rat GFRα-4.

| Exon | Size (bp) | Intron size (bp) | Splice acceptor | Splice donor | Corresponding GFRα-1 exon size (bp) |
|---|---|---|---|---|---|
| 1 | >124 | 560 | — | GAGgtaaggaggt (SEQ ID NO: 36) | — |
| 2 | 355 | 49 | ccctcaccagGGT (SEQ ID NO: 37) | CCGgtgcgtgcgg (SEQ ID NO: 38) | 337 |
| 3 | 110 | 80 | gcgcgcgcagGCC (SEQ ID NO: 39) | TAGgtacgctggg (SEQ ID NO: 40) | 110 |
| 4 | 135 | 741 | gtccctgcagGCA (SEQ ID NO: 41) | TGGgtgagggggc (SEQ ID NO: 42) | 135 |

TABLE 4-continued

Intron-exon structure of rat GFRα-4.

| Exon | Size (bp) | Intron size (bp) | Splice acceptor | Splice donor | Corresponding GFRα-1 exon size (bp) |
|---|---|---|---|---|---|
| 5 | 92 | 139 (varA) 84 (varB) | cactccatagATG (SEQ ID NO: 43) | CGGgtaggtatgg TGGgtgctgtttc (SEQ ID NOS 44 and 45) | 182 |
| 6 | >137 | — | ttgtcccaagGTG ccettctcagGCA (SEQ ID NOS 46 and 47) | — | 753 |

The consensus sequence obtained by removing introns 1 to 4 and intron 5A (sequence 6; variant A) translates into a protein of 273 amino acid residues with a calculated molecular mass of 29.7 kDa and an isoelectric point of 8.92 (sequence 8). The consensus sequence obtained by removing introns 1 to 4 and intron 5B (sequence 7; variant B) translates into a protein of 258 amino acid residues with a calculated molecular mass of 28.0 kDa and an isoelectric point of 8.91 (sequence 9). FIG. 2 shows the alignment of variants A and B of rat GFRα-4. The protein sequences are both similar to the known GFRα sequences and only differ from each other in a small amino acid stretch at the carboxy-terminus. These two sequences probably represent biologically active GFRα-4 variants. Since all the other variants sequenced contain one or more intron sequences, they are probably intermediates of RNA processing. It is not clear why all these intermediates are present in cDNA derived from purified mRNA and why it is so difficult to amplify a cDNA sequence derived from a completely spliced mRNA transcript. GFRα-1 to -4 are characterized by a COOH-terminal sequence typical of a glycosyl-phosphatidyl inositol (GPI)-anchored protein, consisting of a hydrophobic region of 17–31 amino acid residues preceded by a hydrophilic sequence containing a stretch of three small amino acids such as Asp, Cys, Ala, Ser, Gly or Asn (Gerber et al., 1992). The rat GFRα-4 variant A protein sequence has a hydrophobic carboxy-terminus of 21 amino acid residues (position 253 to 273) preceded by two possible GPI cleavage sites (DSS at position 234 to 236 or NAG at position 250–252). Variant B has a shorter hydrophilic carboxy-terminus, implying that no GPI-anchoring is possible for this variant. This could mean that variant B is a soluble form of the rat GFRα-4 receptor. A predicted signal peptide of 29 amino acids is present in both variants (as determined by the SPScan program included in the GCG package; score 7.0, probability 1.171e–02). In addition, one possible site for N-linked glycosylation (NVS at position 192 to 194 in the protein) is present.

Figure 3:
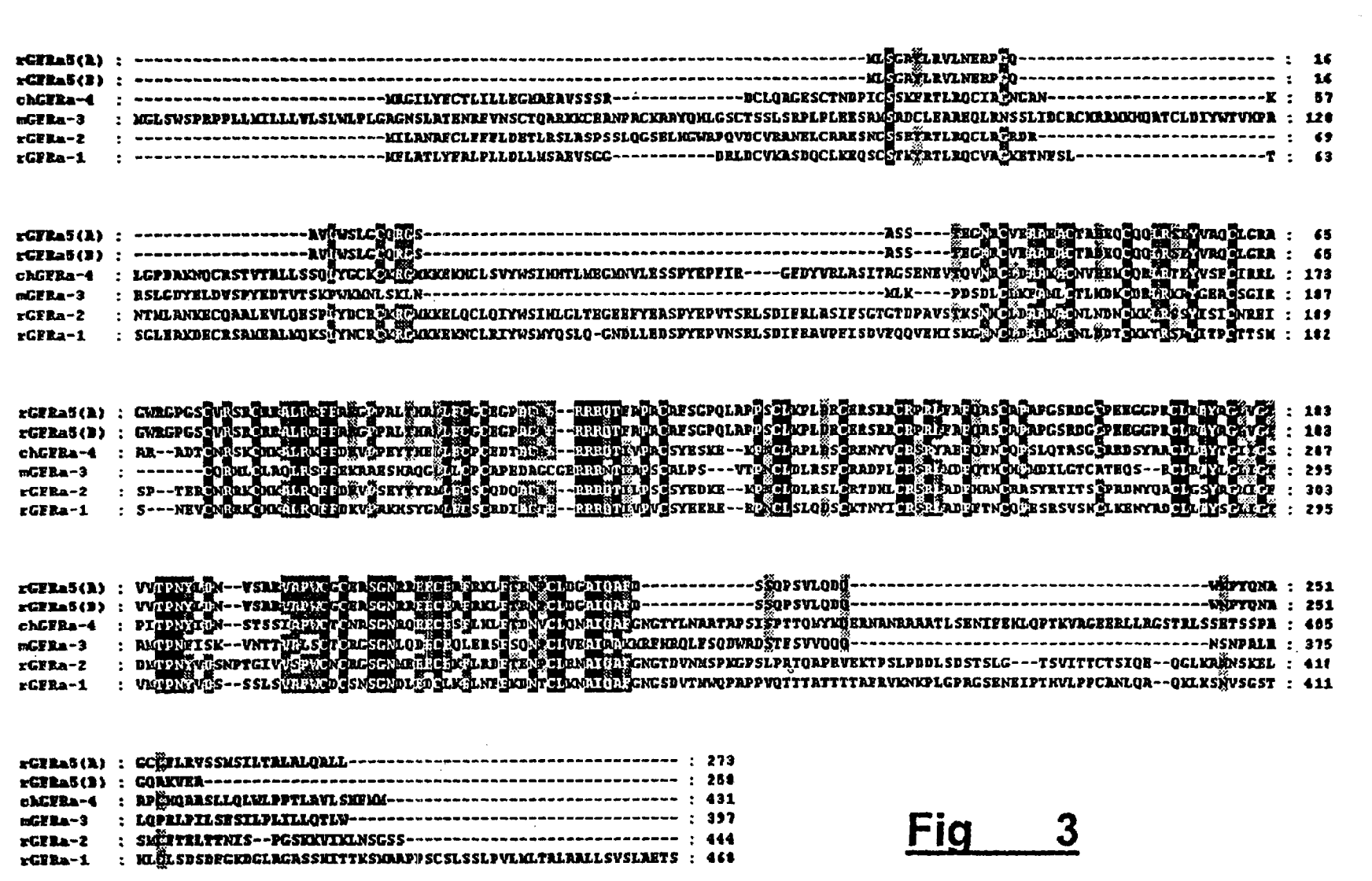

Recently, a model has been proposed for the domain structure of GFRα's based on the comparison of the sequences of mouse GFRα-1 to -3 and chicken GFRα-4 (Airaksinen et al., 1999). The model includes three conserved cysteine-rich domains joined together by less conserved adaptor sequences. The molecules are anchored to the membrane by a GPI-anchor. Rat GFRα-4 conforms partly to this model, since it also contains the second and third cysteine-rich region and a possible GPI-anchor (at least for variant A). However, it differs significantly from the other GFRα's in that the first cysteine-rich region is absent. FIG. 3 shows the alignment of rat GFRα-4 variants A and B with rat GFRα-1 (EMBL acc. no. U59486), rat GFRα-2 (EMBL acc. no. AF003825), mouse GFRα-3 (EMBL acc. no. AB008833) and chicken GFRα-4 (EMBL acc. no. AF045162). The alignment was done using the ClustalW alignment program (EMBL, Heidelberg, Germany). The percentage identity and percentage similarity between members of the GFRα family were calculated by pairwise comparison of the sequences using the GeneDoc software tool (version 2.5.000) and the results are presented in Table 5 below.

TABLE 5

% identity and % similarity (between brackets) between members of the GFRα family. Accession numbers of the sequences used in the analysis are mentioned in the text.

| | rGFRα-1 | rGFRα-2 | mGFRα-3 | cGFRα-4 | rGFRα-4(A) | rGFRα-4(B) |
|---|---|---|---|---|---|---|
| RGFRα-1 | 100 | 43 (60) | 15 (23) | 38 (55) | 20 (29) | 20 (28) |
| rGFRα-2 | | 100 | 18 (28) | 40 (56) | 21 (32) | 21 (31) |
| MGFRα-3 | | | 100 | 16 (25) | 22 (30) | 20 (29) |
| CGFRα-4 | | | | 100 | 27 (37) | 26 (35) |
| RGFRα-4(A) | | | | | 100 | 92 (92) |
| RGFRα-4(B) | | | | | | 100 |

Four members of the GDNF family of neurotrophic factors have been identified so far (GDNF, NTN, PSP, EVN/ARTN). All four signal through binding to a specific GPI-linked GFRα receptor (GFRα-1 for GDNF, GFRα-2 for NTN, GFRα-3 for EVN/ARTN and (chicken) GFRα-4 for PSP) in combination with a common transmembrane tyrosine kinase, cRET. GFRα-4, the coreceptor for PSP, has been identified in chicken only and no mammalian counterpart has been found yet.

The similarity between the rat GFRα-4 described in the present application and the chicken GFRα-4 is 37% (27% identity) suggesting that rat GFRα-4 is a novel member of the GFRα family. GFRα-4 could be the mammalian persephin receptor or, alternatively, could be the receptor for an unidentified GDNF family member.

Specific Binding of Persephin to GFRα-4.

Constructs for the expression of soluble GFRα-IgG-Fc fusion proteins were made as follows. cDNA regions of human GFRα-1, GFR□-2 and GFRα-3, chicken GFRα-4 and rat GFRα-4 variant A (coding for amino acid residues 27 to 427, 20 to 431, 28 to 371, 20 to 399 and 29 to 252, respectively), excluding the sequences coding for the signal peptide and for the COOH-terminal hydrophobic region involved in GPI-anchoring, were cloned in-frame in the expression vector Signal pig plus (R&D Systems Europe Ltd, Abingdon, UK). The inserts of all constructs were confirmed by complete DNA sequence analysis. The resulting proteins expressed from these constructs contain a 17 amino acid residue $NH_2$-terminal CD33 signal peptide, the respective GFRα protein region and a 243 amino acid residue COOH-terminal human $IgG_1$-Fc fusion domain. Fusion proteins were expressed in CHO cells and purified as described. Chinese hamster ovary (CHO) cells were routinely cultured in DMEM/F12 medium supplemented with 10% heat inactivated fetal calf serum. Cells were transfected with GFRα-IgGFc fusion constructs using an optimized Lipofectamine Plus method. For this, a total amount of 6.5 μg DNA was incubated with 17.5 μl PLUS reagent in 750 μl serum free medium for 15 min at room temperature. Lipofectamine was diluted 50-fold into serum free culture medium, 750 μl of this mixture was added to the DNA solution. Following a 15 min incubation at room temperature, 3.5 ml serum free medium was added, and the mixture was brought onto the cells (in a 100 mm petridish). The cells were incubated for 3 h at 37° C. in 5% $CO_2$, after which 5 ml of culture medium, containing 20% heat inactivated fetal calf serum, was added. 24 h later, the medium was changed into regular culture medium. Transfection efficiencies using these optimized conditions were typically 50–60%. For permanent transfections the selection medium contained either 800 μg G418 or 800 μg G418 and 800 μg hygromycin. Antibiotic resistant clones were expanded and assayed for expression using specific antibodies. GFRα-IgGFc fusion proteins were purified from the medium of permanently or transiently transfected CHO cells by protein A chromatography. Bound protein was eluted with 0.1 M Na-citrate, pH 3.0 and collected into 1 M Tris buffer, pH 8.4 (dilution ratio 1:6). Protein concentration was estimated by absorbance at 280 nm using an extinction coefficient of 1.5. Surface plasmon resonance (SPR) U.S. Ser. No. 10/019,337, filed Dec. 19, 2001 experiments were performed at 25° C. using a BIACORE 3000 instrument (Biacore AB, Uppsala, Sweden). Sensor chip CM5, the amine coupling kit and buffers used were also obtained from Biacore AB. Recombinant PSP, NTN, EVN/ART and GDNF were used as immobilised ligands. Recombinant human GDNF was obtained from R&D Systems Europe Ltd. (Abingdon, UK). NH2-terminally 6His-tagged (SEQ ID NO: 48) recombinant human NTN, rat PSP and human EVN/ART were produced in *E. coli* as described previously (Creedon et al., 1997). The carboxylated matrix of a CM5 sensor chip was first activated with a 1:1 mixture of 400 mM N-ethyl-N'-(3-dimethylaminopropyl)-carbodiimide and 100 mM N-hydroxy-succinimide for 10 min. Recombinant neurotrophic factors were applied onto the activated surface in 10 mM sodium acetate buffer, pH 4.5 at a flow rate of 5 μl/min. Unreacted carboxyl groups were blocked with 1 M ethanolamine-HCl. For binding experiments, soluble GFRα-IgGFc fusion proteins were superfused using the kinject program at 30 μl/min. Concentrations of GFRα-IgGFc used in kinetic experiments were between 1 and 100 nM in Hepes buffered saline (150 mM NaCl, 3.5 mM EDTA sodium salt, 0.005% polysorbate 20, 10 mM Hepes, pH 7.4). The association of the GFRα receptors to the immobilised ligands was monitored for 3 min and the dissociation for 1 min, followed by regeneration with 10 mM glycine buffer. Dissociation was initiated by superfusion with Hepes buffered saline. To improve the quality of sensor data, double referencing was used (Myszka, 1999). Data were analyzed using a global analysis with the BIACORE evaluation software (version 3.0.1). Global analysis calculates the association rate ($k_a$) and dissociation rate ($k_d$) simultaneously and the apparent equilibrium dissociation constant ($K_D$) is then calculated as $k_d/k_a$. A simple 1:1 Langmuir model was used to fit the data. Specific binding to PSP could be detected with both rat and chicken GFRα-4-IgGFc fusion proteins. The observed binding of GFRα4-IgGFc was specific as there was no binding to GDNF, NTN or EVN/ART. Control experiments confirmed binding of GFR-1 to GDNF, of GFRα-2 to NTN and of GFRα-3 to EVN/ART. From the binding curves obtained using three determinations at differing concentrations of rat and chicken GFRα4-IgGFc, the binding constants ka (association rate) and $k_d$ (dissociation rate) were derived (Table 6).

TABLE 6

Persephin binding to chicken GFRα-4 and rat GFRα-4.
Binding constants for chicken GFRα-4-IgGFc and rat GFRα-4-IgGFc binding to immobilised persephin as determined by SPR. The mean association rate ($k_a$), dissociation rate ($k_d$) and apparent equilibrium dissociation constant ($K_D$) ± standard errors were derived from the binding curves obtained using 3 determinations at differing concentrations of the respective soluble receptors.

|  | $k_a$ (1/Ms) | $k_d$ (1/s) | $K_D$ (M) |
|---|---|---|---|
| chicken GFRα-4 | 2.3 ± 2.6 × $10^4$ | 8.8 ± 5.1 × $10^{-4}$ | 5.4 ± 2.9 × $10^{-9}$ |
| rat GFRα-4 | 2.7 ± 1.6 × $10^4$ | 1.2 ± 0.2 × $10^{-3}$ | 5.9 ± 2.8 × $10^{-9}$ |

Although apparent $K_D$ values were very similar for both fusion proteins, $R_{Max}$ values were significantly different. Binding levels of ~1000 relative units (RU) were routinely obtained with chicken GFRα-4-IgGFc, whereas binding levels of rat GFRα4-IgGFc were approximately 20 times lower, around 50–60 RU. This could be due to differences in the concentration of active chicken GFR-4-IgGFc and rat GFRα-4-IgGFc fusion protein. The calculated equilibrium dissociation constant $K_D$ of 5.9±2.8 nM (n=3) suggests that rat GFRα-4 is a receptor specific for persephin.

Northern Blot Analysis.

Northern blots containing 2 μg of poly(A)-rich RNA derived from different rodent tissues (mouse MTN™ blot, mouse embryo MTN™ blot and rat MTN™ blot; Clontech Laboratories) were hybridized according to the manufacturer's instructions with a α-[$^{32}$P]-dCTP random-priming labeled (HighPrime kit, Roche Diagnostics) 948 bp fragment derived from the rat GFRα-4 coding sequence (as in sequence ID No. 6). Stringency washes were performed in 0.1×SSC/0.1% SDS at 50° C. (the two mouse blots) or 55°

Figure 4:
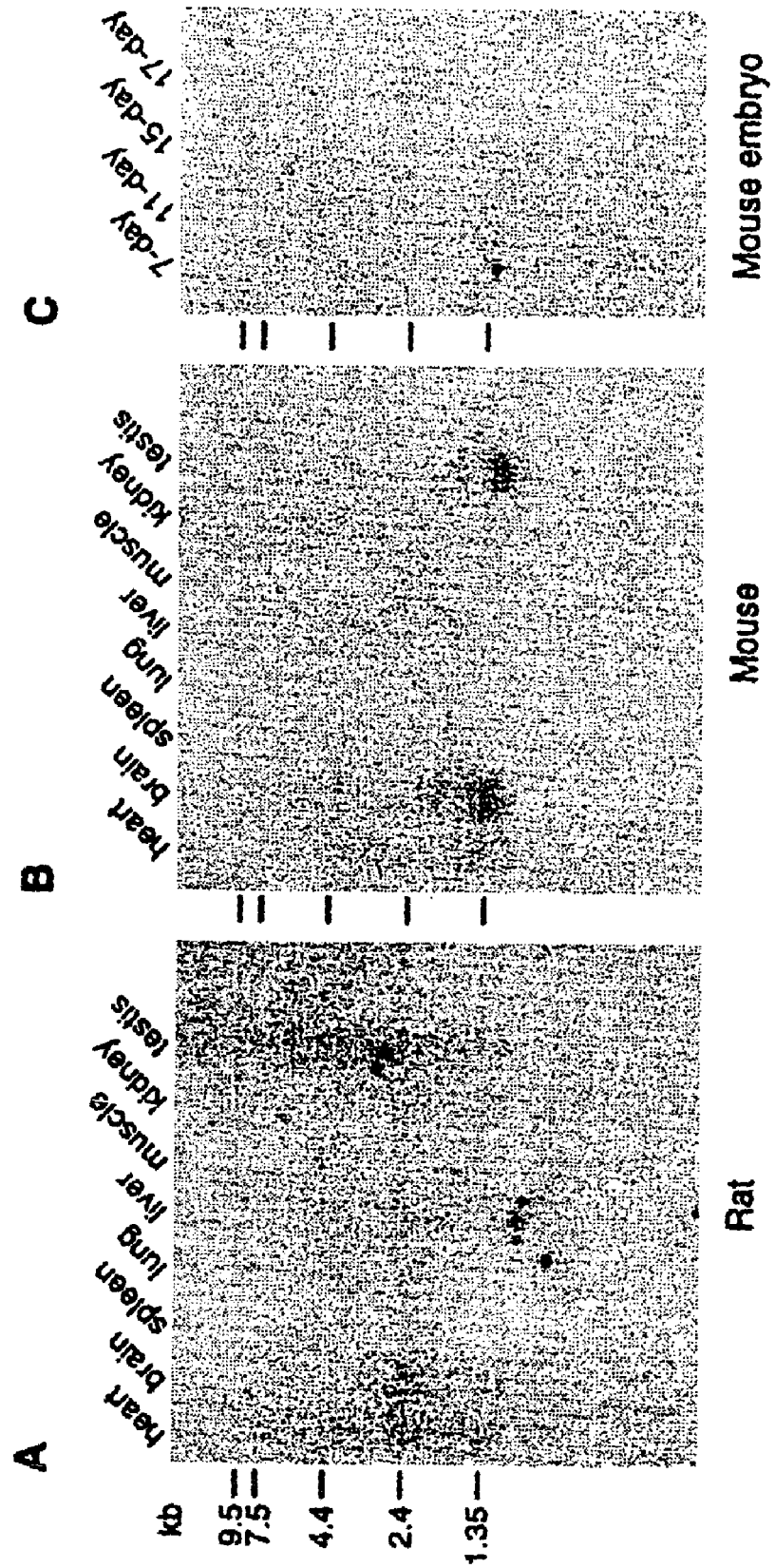
FIG. 4: Northern blot analysis of rodent GFRα-4 mRNA expression. The expression of rat and mouse GFRα-4 mRNA in different tissues was assessed using a probe corresponding to the coding sequence of rat GFRα-4 to analyze blots of poly(A)-rich RNA. (A) Rat Multiple Tissue Northern (MTN) blot; (B) Mouse MTN blot and (C) Mouse Embryo MTN blot. Apparent sizes are indicated (in kilobase pairs) by horizontal lines to the left of each panel.

C. (the rat blot). The results are shown in FIG. 4. In rat, a very weak signal could be detected around 2.3 kb in heart, brain, liver and testis. An even weaker second transcript was present around 1.4 kb in the same tissues. In mouse, a 1.35 kb transcript was most intense in brain and testis, with a much weaker signal present around 2 kb. Very low mRNA expression of the 1.35 kb transcript was also present in 15-day and 17-day mouse embryo. The size of the smaller transcript is in agreement with the predicted size of the GFRα-4 coding sequence (±880 bp+the 3' untranslated region of 570 bp).

Chromosomal Localization of Rat, Mouse and Human GFRα-4.

A 0.95 kb rat GFRα-4 cDNA fragment (containing the full rat GFRα-4 coding sequence of variant A) and a 2.3 kb fragment corresponding to the rat GFRα-4 genomic sequence (see sequence ID No. 5) were used as probes in fluorescent in situ hybridization (FISH) analysis on rat chromosomes. These probes were partially overlapping. A mixture of the two probes (1 µg total DNA) was labeled with digoxigenin-11-dUTP (Roche Diagnostics, Mannheim, Germany) by nick translation (Life Technologies) producing a final probe fragment size of 200–400 bp. The labeled probe was mixed with hybridization buffer (50% formamide, 2×SSC, 10% dextran sulfate). After denaturation, the mixture was placed on metaphase rat chromosome slides (Islam and Levan, 1987, Helou et al., 1998) denatured at 72° C. for 2 min in 70% formamide, 2×SSC. After hybridization for 48 h at 37° C., preparations were washed for 15 min in 50% formamide, 2×SSC. Detection of labeled chromosomes was done by standard FITC anti-digoxigenin. Chromosome spreads were counterstained with 4', 6-diamidino-2-phenylindole (DAPI). Results were derived from micrographs of 100 different cells. Due to the small size of the probes there was considerable background. However, most studied cells showed label at position RNO3q36 (FIG. 5). About 35% of the metaphase studies showed "double spot" label at both homologues of RNO3, whereas about 50% had double spots on only one of the homologues or "single spot" label on both homologues. No other chromosomal site showed label in several cells. Based on comparative mapping, the corresponding mouse locus would be expected to be located at MMU2 (band F), whereas a possible human location for the gene would be HSA2, HSA15 or HSA20. In agreement with this, the genomic mouse and human GFRα-4 sequences identified in the EMBL database (Accession No. AF155960 for mouse and AC017113 for human) are derived from mouse chromosome 2 (BAC clone 389B9) and from human chromosome 2 (EMBL accession number AC013324; BAC388_K_24map2), respectively.

REFERENCES

Airaksinen, M. S., Titievsky, A. & Saarma, M. (1999) GDNF family neurotrophic factor signaling: four masters, one servant? *Mol. Cell. Neurosci.* 13, 313–325.

Altschul, S. F., Gish, W., Miller, W., Myers, E. W. & Lipman, D. J. (1990) Basic local alignment search tool, *J. Mol. Biol.* 215, 403–410.

Angrist, M., Jing, S., Bolk, S., Bentley, K., Nallasamy, S., Halushka, M., Fox, G. M. & Chakravarti, A. (1998) Human GFRα1: cloning, mapping, genomic structure, and evaluation as a candidate gene for Hirschsprung disease susceptibility. *Genomics* 48, 354–362.

Baloh, R. H., Tansey, M. G., Golden, J. P., Creedon, D. J., Heuckeroth, R. O., Keck, C. L., Zimonjic, D. B., Popescu, N. C., Johnson, E. M. & Milbrandt, J. (1997) TrnR2, a novel receptor that mediates neurturin and GDNF signaling through Ret. *Neuron* 18, 793–802.

Baloh, R. H., Gorodinsky, A., Golden, J. P., Tansey, M. G., Keck, C. L., Popescu, N. C., Johnson, E. M. & Milbrandt, J. (1998a) GFRα3 is an orphan member of the GDNF/neurturin/persephin receptor family. *Proc. Natl. Acad. Sci. USA* 95, 5801–5806.

Baloh, R. H., Tansey, M. G., Lampe, P. A., Fahrner, T. J., Enomoto, H., Simburger, K. S., Leitner, M. L., Araki, T., Johnsson, E. M. & Milbrandt, J. (1998b) Artemin, a novel member of the GDNF ligand family, supports peripheral and central neurons and signals through the GFRα-3-RET receptor complex. *Neuron* 21, 1291–1302.

Beck, K. D., Valverde, J., Alexi, T., Poulsen, K., Moffat, B., Vandlen, R A., Rosenthal, A. & Hefti, F. (1995) Mesencephalic dopaminergic neurons protected by GDNF from axotomy-induced degeneration in the adult brain. *Nature* 373,339–341.

Bilang-Bleuel, A., Revah, F., Colin, P., Locquet, I., Robert J. J., Mallet, J. & Horellou, P. (1997) Intrastriatal injection of an adenoviral vector expressing glial-cell-line-derived neurotrophic factor prevents dopaminergic neuron degeneration and behavioral impairment in a rat model of Parkinson disease. *Proc. Natl. Acad. Sci. USA* 94, 8818–8823.

Buj-Bello, A., Buchman, V. L., Horton, A., Rosenthal, A. & Davies A. M. (1995) GDNF is an age-specific survival factor for sensory and autonomic neurons. *Neuron* 15, 821–828.

Buj-Bello, A., Adu, J., Piñòn, L. G. P., Horton, A., Thompson, J., Rosenthal, A., Chinchetru, M., Buchman, V. L. & Davies, A. M. (1997) Neurturin responsiveness requires a GPI-linked receptor and the Ret receptor tyrosine kinase. *Nature* 387, 721–724.

Choi-Lundberg, D. L., Lin, Q., Chang, Y. N., Chiang, Y. L., Hay, C. M., Mohajeri, H., Davidson, B. L. & Bohn, M. C. (1997) Dopaminergic neurons protected from degeneration by GDNF gene therapy. *Science.* 275, 838–841.

Creedon, D. J., Tansey, M. G., Baloh, R. H., Osborne, P. A., Lampe, P. A., Fahrner, T. J., Heuckeroth, R. O., Milbrandt, J. & Johnson, E. M. (1997) Neurturin shares receptors and signal transduction pathways with glial cell line-derived neurotrophic factor in sympathetic neurons. *Proc. Natl. Acad. Sci. USA,* 94, 7018–7023.

Durbec, P., Marcos-Gutierrez, C. V., Kilkenny, C., Grigoriou, M., Wartiowaara, K., Suvanto, P., Smith, D., Ponder, B., Costantini, F., Saarma, M., Sariola, H. & Pachnis, V. (1996) GDNF signalling through the RET receptor tyrosine kinase. *Nature* 381, 789–793.

Enokido, Y., de Sauvage, F., Hongo, J.-A., Ninkina, N., Rosenthal, A., Buchman, V. L. & Davies, A. M. (1998) GFRα-4 and the tyrosine kinase Ret form a functional receptor complex for persephin. *Current Biology* 8, 1019–1022.

Gash, D. M., Zhang, Z., Ovadia, A., Cass, W. A., Yi, A., Simmerman, L., Russell, D., Martin, D., Lapchak, P. A., Collins, F., Hoffer, B. J. & Gerhardt, G. A. (1996) Functional recovery in parkinsonian monkeys treated with GDNF. *Nature* 380, 252–255.

Gerber, L. D., Kodukula, K. & Udenfriend, S. (1992) Phosphatidylinositol glycan (PI-G) anchored membrane proteins. *J. Biol. Chem.* 267, 12168–12173.

GFRα Nomenclature Committee (1997) Nomenclature of GPI-linked receptors for the GDNF ligand family. *Neuron* 19, 485.

Helou, K., Walther, L., Günther, E., Klinga-Levan, K. & Levan, G. (1998) Cytogenetic orientation of the rat major histocompatibility complex (MHC) on chromosome 20. *Immunogenetics* 47:166–169.

Henderson, C. E., Phillips, H. S., Pollock, R. A., Davies, A. M., Lemeulle, C., Armanini, M., Simmons, L., Moffet, B., Vandlen, R. A., Koliatsos, V. E. & Rosenthal, A. (1994) GDNF: a potent survival factor for motoneurons present in peripheral nerve and muscle. *Science* 266, 1062–1064.

Islam, M. Q. & Levan, G. (1987) A new fixation procedure for improved quality G-bands in routine cytogenetic work. *Hereditas* 107:127–130.

Jing, S., Wen, D., Yu, Y., Holst, P. L., Luo, Y., Fang, M., Tamir, R., Antonio, L., Hu, Z., Cupples, R., Louis, J.-C., Hu, S., Altrock, B. W. & Fox, G. M. (1996) GDNF-induced activation of the ret protein tyrosine kinase is mediated by GDNFR-α, a novel receptor for GDNF. *Cell* 85, 1113-1124.

Jing, S., Yu, Y., Fang, M., Hu, Z., Holst, P. L., Boone, T., Delaney, J., Schultz, H., Zhou, R. & Fox, G. M. (1997) GFRα-2 and GFRα-3 are two new receptors for ligands of the GDNF family. *J. Biol. Chem.* 272, 33111–33117.

Kingsley, D. M. (1994) The TGF-beta superfamily: new members, new receptors, and new genetic tests of function in different organisms. *Genes & Development* 8, 133–146.

Klein, R. D., Sherman, D., Ho, W.-H., Stone, D., Bennett, G. L., Moffat, B., Vandlen, R., Simmons, L., Gu, Q., Hongo, J.-A., Devaux, B., Poulsen, K., Armanini, M., Nozaki, C., Asai, N., Goddard, A., Phillips, H., Henderson, C. E., Takahashi, M. & Rosenthal, A. (1997) A GPI-linked protein that interacts with Ret to form a candidate neurturin receptor. *Nature* 387, 717–721.

Kotzbauer, P. T., Lampe, P. A., Heuckeroth, R. O., Golden, J. P., Creedon, D. J., Johnson, E. M. & Milbrandt, J. (1996) Neurturin, a relative of glial-cell-line-derived neurotrophic factor. *Nature* 384, 467–470.

Lin, L.-F. H., Doherty, D. H., Lile, J. D., Bektesh, S. & Collins, F. (1993) GDNF: a glial cell line-derived neurotrophic factor for midbrain dopaminergic neurons. *Science* 260, 1130–1132.

Mandel, R. J., Spratt, S. K., Snyder, R. O. & Leff, S. E. (1997) Midbrain injection of recombinant adeno-associated virus encoding rat glial cell line-derived neurotrophic factor protects nigral neurons in a progressive 6-hydroxy-dopamine-induced degeneration model of Parkinson's disease in rats. *Proc. Natl. Acad. Sci. USA* 94, 14083–14088.

Masure, S., Cik, M., Pangalos, M. N., Bonaventure, P., Verhasselt, P., Lesage, A. S., Leysen, J. E. & Gordon R. D. (1998) Molecular cloning, expression and tissue distribution of glial-cell-line-derived neurotrophic factor family receptor α-3 (GFRα-3). *Eur. J. Biochem.* 251, 622–630.

Masure, S., Geerts, H., Cik, M., Hoefnagel, E., Tuytelaars, A., Harris, S., Lesage, A. S. J., Leysen, J. E., van der Helm, L., Verhasselt, P., Yon, J. & Grodon, R. D. (1999) Enovin, a novel member of the GDNF family of neurotrophic growth factors with growth promoting and neuroprotective effects on neuronal cells. Masure et al., (1999) Eur. J. Biochem. 266:892–902.

Milbrandt, J., de Sauvage, F. J., Fahrner, T. J., Baloh, R. H., Leitner, M. L., Tansey, M. G., Lampe, P. A., Heuckeroth, R. O., Kotzbauer, P. T., Simburger, K. S., Golden, J. P., Davies, J. A., Vejsada, R., Kato, A. C., Hynes, M., Sherman, D., Nishimura, M., Wang, L. C., Vandlen, R., Moffat, B., Klein, R. D., Poulsen, K., Gray, C., Garces, A., Henderson, C. E., Phillips, H. S. & Johnson, E. M. Jr. (1998) Persephin, a novel neurotrophic factor related to GDNF and neurturin. *Neuron* 20, 245–253.

Mount, H. T., Dean, D. O., Alberch, J., Dreyfus, C. F. & Black, I. B. (1995) Glial cell line-derived neurotrophic factor promotes the survival and morphologic differentiation of Purkinje cells. *Proc. Natl. Acad. Sci. USA* 92, 9092–9096.

Myszka, D. G. (1999) Improving biosensor analysis. *J. Mol. Recognit.* 12, 279–284.

Naveilhan, P., Baudet, C., Mikaels, A., Shen, L., Westphal, H. & Ernfors, P. (1998) Expression and regulation of GFRα3, a glial cell line-derived neurotrophic factor family receptor. *Proc. Natl. Acad. Sci. USA* 95, 1295–1300.

Oppenheim, R. W., Houenou, L. J., Johnson, J. E., Lin, L. F., Li, L., Lo, A. C., Newsome, A. L., Prevette, D. M. & Wang, S. (1995) Developing motor neurons rescued from programmed and axotomy-induced cell death by GDNF. *Nature* 373, 344–346.

Sanicola, M., Hessiono, C., Worley, D., Carmillo, P., Ehrenfels, C., Walus, L., Robinson, S., Jaworski, G., Wei, H., Tizard, R., Whitty, A., Pepinsky, R. B. & Cate, R. L. (1997) Glial cell line-derived neurotrophic factor-dependent RET activation can be mediated by two different cell-surface accessory proteins. *Proc. Natl. Acad. Sci. USA* 94, 6238–6243.

Senaphthy, P., Shapiro, M. B. & Harris, N. L. (1990) Splice junctions, branch point sites, and exons: sequence statistics, identification, and applications to genome project. *Methods Enzymol.* 183, 252–278.

Suvanto, P., Wartiovaara, K., Lindahl, M., Arumäe, U., Moshnyakov, M., Horelli-Kuitunen, N., Airaksinen, M. S., Palotie, A., Sariola, H. & Saarma, M. (1997) Cloning, mRNA distribution and chromosomal localisation of the gene for glial cell line-derived neurotrophic factor receptor β, a homologue to GDNFR-α. *Human Mol. Genet.* 6, 1267–1273.

Thompson, J., Doxakis, E., Piñòn, L. G. P., Strachan, P., Buj-Bello, A., Wyatt, S., Buchman, V. L. & Davies, A. M. (1998) GFRα-4, a new GDNF family receptor. *Mol. Cell. Neurosci.* 11, 117–126.

Tomac, A., Lindqvist, E., Lin, L. F., Ogren, S. O., Young, D., Hoffer, B. J. & Olson, L. (1995) Protection and repair of the nigrostriatal dopaminergic system by GDNF in vivo. *Nature* 373, 335–339.

Treanor, J. J. S., Goodman, L., de Sauvage, F., Stone, D. M., Poulsen, K. T., Beck, C. D., Gray, C., Armanini, M. P., Pollock, R. A., Hefti, F., Phillips, H. S., Goddard, A., Moore, M. W., Buj-Bello, A., Davies, A. M., Asai, N., Takahashi, M., Vandlen, R., Henderson, C. E. & Rosenthal, A. (1996) Characterization of a multicomponent receptor for GDNF. *Nature* 382, 80–83.

Trupp, M., Arenas, E., Fainzilber, M., Nilsson, A. S., Sieber, B. A., Grigoriou, M., Kilkenny, C., Salazar-Grueso, E., Pachnis, V., Arumäe, U., Sariola, H., Saarma, M. & Ibanez, C. F. (1996) Functional receptor for GDNF encoded by the c-ret proto-oncogene. *Nature* 381, 785–788.

Widenfalk, J., Nosrat, C., Tomac, A., Westphal, H., Hoffer, B. & Olson, L. (1997) Neurturin and glial cell line-derived neurotrophic factor receptor-β (GDNFR-β), novel proteins related to GDNF and GDNFR-α with specific cellular patterns of expression suggesting roles in the developing and adult nervous system and in peripheral organs. *J. Neurosci.* 17, 8506–8519.

Widenfalk, J., Tomac, A., Lindqvist, E., Hoffer, B. & Olson, L. (1998) GFRα-3, a protein related to GFRα-1, is expressed in developing peripheral neurons and ensheathing cells. *Eur. J. Neurosci.* 10, 1508–1517.

Worby, C. A., Vega, Q. C., Zhao, Y., Chao, H. H.-J., Seasholtz, A. F. & Dixon, J. E. (1996) Glial cell line-derived neurotrophic factor signals through the RET receptor and activates mitogen-activated protein kinase. *J. Biol. Chem.* 271, 23619–23622.

Worby, C. A., Vega, Q. C., Chao, H. H. J., Seasholtz, A. F., Thompson, R. C. & Dixon J. E. (1998) Identification and characterization of GFRα-3, a novel co-receptor belonging to the glial cell line-derived neurotrophic receptor family. *J. Biol. Chem.* 273, 3502–3508.

Yan, Q., Matheson, C. & Lopez, O. T. (1995) In vivo neurotrophic effects of GDNF on neonatal and adult facial motor neurons. *Nature* 373, 341–344.

| List of abbreviations | |
|---|---|
| ARTN | artemin |
| BLAST | basic local alignment search tool |
| bp | base pairs |
| cDNA | complementary DNA |
| CNS | central nervous system |
| EST | expressed sequence tag |
| EVN | enovin |
| GDNF | glial cell-line derived neurotrophic factor |
| GFRα | GDNF family receptor α |
| GPI | glycosyl phosphatidyl inositol |
| NTN | neurturin |
| PCR | polymerase chain reaction |
| PNS | peripheral nervous system |
| PSP | persephin |
| SSP | smallest sum probability |
| TGF-β | transforming growth factor β |

The invention claimed is:

1. An isolated and purified GFRα-4 receptor polypeptide comprising SEQ ID NO: 9.

* * * * *